(12) United States Patent
Zreiqat et al.

(10) Patent No.: US 9,220,806 B2
(45) Date of Patent: Dec. 29, 2015

(54) BIOCOMPATIBLE MATERIAL AND USES THEREOF

(75) Inventors: Hala Zreiqat, Chatswood (AU); Seyed-Iman Roohani-Esfahani, Newtown (AU); Colin Dunstan, Beecroft (AU); Jiao Jiao Li, Marrickville (AU)

(73) Assignee: The University of Sydney, New South Wales (AU)

( * ) Notice: Subject to any disclaimer, the term of this patent is extended or adjusted under 35 U.S.C. 154(b) by 44 days.

(21) Appl. No.: 14/122,757

(22) PCT Filed: Jun. 1, 2012

(86) PCT No.: PCT/AU2012/000625
§ 371 (c)(1),
(2), (4) Date: Nov. 27, 2013

(87) PCT Pub. No.: WO2012/162753
PCT Pub. Date: Dec. 6, 2012

(65) Prior Publication Data
US 2014/0105940 A1 Apr. 17, 2014

(30) Foreign Application Priority Data

Jun. 1, 2011 (AU) .............................. 2011902160
Sep. 23, 2011 (AU) .............................. 2011903923

(51) Int. Cl.
| | | |
|---|---|---|
| *A61L 27/10* | (2006.01) | |
| *A61L 27/56* | (2006.01) | |
| *C04B 41/83* | (2006.01) | |
| *C04B 35/22* | (2006.01) | |
| *C04B 35/624* | (2006.01) | |
| *C04B 35/626* | (2006.01) | |
| *C04B 41/00* | (2006.01) | |
| *C04B 41/48* | (2006.01) | |
| *A61L 27/30* | (2006.01) | |
| *A61L 27/34* | (2006.01) | |
| *A61L 27/42* | (2006.01) | |
| *A61K 33/06* | (2006.01) | |
| *A61K 33/24* | (2006.01) | |
| *A61K 33/30* | (2006.01) | |
| *C04B 38/00* | (2006.01) | |
| *C04B 111/00* | (2006.01) | |

(52) U.S. Cl.
CPC ................ *A61L 27/10* (2013.01); *A61K 33/06* (2013.01); *A61K 33/24* (2013.01); *A61K 33/30* (2013.01); *A61L 27/306* (2013.01); *A61L 27/34* (2013.01); *A61L 27/427* (2013.01); *A61L 27/56* (2013.01); *C04B 35/22* (2013.01); *C04B 35/624* (2013.01); *C04B 35/62685* (2013.01); *C04B 38/0045* (2013.01); *C04B 41/009* (2013.01); *C04B 41/48* (2013.01); *C04B 41/83* (2013.01); *A61L 2420/04* (2013.01); *A61L 2430/02* (2013.01); *A61L 2430/12* (2013.01); *C04B 2111/00836* (2013.01); *C04B 2235/3206* (2013.01); *C04B 2235/3213* (2013.01); *C04B 2235/3215* (2013.01); *C04B 2235/3217* (2013.01); *C04B 2235/3222* (2013.01); *C04B 2235/3272* (2013.01); *C04B 2235/3284* (2013.01); *C04B 2235/3481* (2013.01); *C04B 2235/80* (2013.01); *C04B 2235/96* (2013.01)

(58) Field of Classification Search
CPC . A61K 2800/884; A61K 6/0612; A61K 8/35; A61K 8/43; A61K 8/44; A61K 8/447; A61K 8/4913; A61K 8/97; A61L 27/10; A61L 27/306; A61L 31/026; A61L 31/088
See application file for complete search history.

(56) References Cited

U.S. PATENT DOCUMENTS

| | | | |
|---|---|---|---|
| 3,787,900 | A | 1/1974 | McGee |
| 5,210,057 | A | 5/1993 | Haun et al. |
| 6,162,537 | A | 12/2000 | Martin et al. |
| 7,410,921 | B2 | 8/2008 | Pinckney et al. |
| 2009/0093571 | A1 | 4/2009 | Towler et al. |
| 2011/0111005 | A1 | 5/2011 | Zreiqat et al. |

FOREIGN PATENT DOCUMENTS

| | | |
|---|---|---|
| WO | WO 2006/047820 | 11/2005 |
| WO | WO 2010/003191 | 1/2010 |

OTHER PUBLICATIONS

Cordioli et al., "Maxillary Sinus Floor Augmentation Using Bioactive Glass Granules and Autogenous Bone with Simultaneous Implant Placement: Clinical and Histological Findings", Clin. Oral Implants Res., Jun. 2001, 12(3), 270-278.
Gorustovich et al., "Osteoconductivity of Strontium-Doped Bioactive Glass Particles: A Histomorphometric Study in Rats", Journal of Biomedical Materials Research Part A, Jan. 2010, 92(1), 232-237.
Graves et al., "The Australian Orthopaedic Association National Joint Replacement Registry", Medical Journal of Australia, Mar. 1, 2004, 180 (Suppl5), S31-S34.
Hench, "Bioceramics", J. Am. Ceram. Soc., Jul. 1998, 81, 1705-1728.
Hoppe et al., "A Review of the Biological Response to Ionic Dissolution Products From Bioactive Glasses and Glass-Ceramics", Biomaterials, Feb. 2, 2011, 32, 2757-2774.

(Continued)

*Primary Examiner* — Audrea Buckley
(74) *Attorney, Agent, or Firm* — Baker & Hostetler LLP

(57) ABSTRACT

The present invention relates to a biocompatible material and in particular to a two-phase or composite biocompatible ceramic material, wherein the first phase is a doped calcium zinc silicate and the second phase is a metal oxide. In an embodiment, the invention has been developed for use in tissue regeneration including bone tissue. In other embodiments, the invention has been developed as a coating to improve the long-term stability of prior art implantable medical devices.

23 Claims, 24 Drawing Sheets

(56) References Cited

OTHER PUBLICATIONS

Kokubo, T. and Takadama H., "How Useful is SBF in Predicting In Vivo Bone Bioactivity," Biomaterials Jan. 31, 2006, 27, 2907-2915.

Roohani-Esfahani et al., "The Influence Hydroxyapatite Nanoparticle Shape and Size on the Properties of Biphasic Calcium Phosphate Scaffolds Coated with Hydroxyapatite-PCL Composites", Biomaterials, Jul. 2010, 31(221), 5498-5509.

Siriphannon et al., "Formulation of Hydroxyapatite on $CaSiO_3$ Powders in Simulated Body Fluid", Journal of the European Ceramic Society, Apr. 2002, 22(4), 511-520.

Tay et al., "Calcium Sulfate and Calcium Phosphate Based Bone Substitutes, Mimicry of the Mineral Phase of Bone", Orthop. Clin. North Am., Oct. 4, 1999, 30(4), 615-623.

Wiltfang et al., "Degradation Characteristics of $\alpha$ and $\beta$ Tri-Calcium-Phosphate (TCP) in Minipigs", Journal of Biomedical Materials Research, 2002, 63(2), 115-121.

Wu et al., "The Effect of Zn Contents on Phase Composition, Chemical Stability and Cellular Bioactivity in Zn—Ca—Si System Ceramics", Journal of Biomedical Materials Research Part B: Applied Biomaterials, May 17, 2008, 87B(2), 346-353.

Xynos et al., "Ionic Products of Bioactive Glass Dissolution Increase Proliferation of Human Osteoblasts and Induce Insulin-Like Growth Factor II mRNA Expression and Protein Synthesis", Biochemical and Biophysical Research Communications, Sep. 24, 2000, 276(2), 461-465.

Yaszemski et al., "Evolution of Bone Transplantation: Molecular, Cellular and Tissue Strategies to Engineer Human Bone", Biomaterials, 1996, 17(2), 175-185.

Zreiqat et al., "The Incorporation of Strontium and Zinc into Calcium—Silicon Ceramic for Bone Tissue Engineering", Biomaterials, Feb. 2010, 31(12), 3175-3184.

| Days | Ions | Ion concentration(ppm) | pH | Weight decrease(%) |
|---|---|---|---|---|
| 1 | Ca | 4.9 | 7.43 | 1.1 |
|   | Si | 0.1 |   |   |
|   | Zn | 0.01 |   |   |
|   | Sr | 0.05 |   |   |
|   | Al | 0 |   |   |
| 7 | Ca | 5.6 | 7.41 | 1.00 |
|   | Si | 0.1 |   |   |
|   | Zn | 0.01 |   |   |
|   | Sr | 0.03 |   |   |
|   | Al | 0 |   |   |
| 14 | Ca | 6.4 | 7.40 | 1.4 |
|   | Si | 0.2 |   |   |
|   | Zn | 0.005 |   |   |
|   | Sr | 0.12 |   |   |
|   | Al | 0 |   |   |
| 28 | Ca | 9.1 | 7.33 | 2.1 |
|   | Si | 0.2 |   |   |
|   | Zn | 0.002 |   |   |
|   | Sr | 0.13 |   |   |
|   | Al | 0 |   |   |

FIGURE 5

BIOCOMPATIBLE MATERIAL AND USES THEREOF

CROSS-REFERENCE TO RELATED APPLICATIONS

This application is the National Stage of International Application No. PCT/AU2012/000625, filed Jun. 1, 2012, which claims the benefit of Australian Application No. 2011902160, filed Jun. 1, 2011, and Australian Application No. 2011903923, filed Sep. 23, 2011, the disclosures of which are incorporated herein by reference in their entireties.

FIELD OF THE INVENTION

The present invention relates to a biocompatible material and in particular to a two-phase or composite biocompatible ceramic material, wherein the first phase is a doped calcium zinc silicate and the second phase is a metal oxide. In one embodiment, the invention has been developed for use in tissue regeneration including bone tissue. In other embodiments, the invention has been developed as a coating to improve the long-term stability of prior art implantable medical devices. In another embodiment, the invention has been developed for use in drug delivery or for skeletal tissue regeneration. In another embodiment, the invention has been developed for delivery in an injectable form. However, it will be appreciated that the invention is not limited to these particular fields of use.

BACKGROUND OF THE INVENTION

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Bone, as a living tissue, has the ability to heal itself, however in some cases damage to the bone from whatever cause is too severe to allow natural healing to take place, and so a bone graft is required to stimulate regeneration. There are three main types of bone grafts: autografts, allografts and synthetic grafts. Significant research is being conducted in the field of synthetic grafts as bone substitutes since synthetic grafts can ameliorate many of the problems associated with autografts and allografts, such as limited supply, donor site pain, and immunogenicity issues.

In the case of advanced degenerative bone disease, joint replacement therapy remains the only treatment available for relieving the pain and suffering. However, the technologies available in this area of orthopaedics are far from satisfactory. For example, Australians require more than sixty-thousand hip and knee replacement operations annually, a rate that has been estimated to be increasing by some 10% per annum, and a staggering 25% of which are revisions of failed implants [Graves, S. E., et al., The Australian Orthopaedic Association National Joint Replacement Registry. Med. J. Aust., 2004; 180 (5 Suppl): p.S31-4]. Further complications arise in situations where bone stock is compromised, or where initial implant stability is questionable (e.g., elderly patients, post-traumatic injuries or in revision operations), in which cases short- and long-terms clinical results are typically inferior. The increases in life expectancy, and in the number of younger patients requiring implants, highlights the need for greater implant longevity and has driven biomedical research to develop novel micro-engineered surfaces to anchor the cementless prosthesis directly to the living bone through osteo-integration, thereby attempting to provide a stable interface strong enough to support life-long functional loading. It is clear that there is a serious problem with the longevity of current orthopaedic devices; a problem that is anticipated to only increase with the increasing demand from the aging population requiring such treatments. It is clear that any improvement that could be made to increase the performance of these orthopaedic devices would be welcomed, not only by the orthopaedic community but also by the patients themselves.

3D scaffolds that promote the migration, proliferation and differentiation of bone and endothelial cells are becoming increasingly important in not only orthopaedic but also maxillofacial surgery. An ideal bone replacement material should support bone formation and vascularisation; show minimal fibrotic reaction and serve as a temporary biomaterial for bone remodeling. They must also degrade in a controlled fashion into non-toxic products that the body can metabolise or excrete via normal physiological mechanisms (Yaszemski, et al., Biomaterials, 1996, 17, pp. 175-185). Scaffolds need to be mechanically strong and matched with a similar modulus of elasticity to that of bone in order to prevent stress shielding as well as maintaining adequate toughness to prevent fatigue fracture under cyclic loading. At present there are no successful strategies available for bone tissue regeneration and resurfacing arthritic joints with articular cartilage. The lack of cartilage reparative response creates a great demand for new modalities that promote tissue regeneration.

Over the last century, various ceramics have been investigated for the purpose of encouraging or stimulating bone growth and as scaffolds. For example, in the 1880s calcium sulfate (plaster of Paris) was utilised. However, calcium sulfate displays a relatively low bioactivity and a relatively high rate of degradation (Tay, et al., Orthop. Clin. North Am., 1999, 30:615-23). In the 1950s hydroxyapatite was utilised, but it suffers from a relatively low degradation rate and poor mechanical properties (Wiltfang J., et al J. Biomed. Mater. Res. 2002;63:115-21). In the 1970s Bioglass® was developed. However, this material it is relatively hard to handle due to its inherent brittleness and has a relatively low bending strength (Cordioli G., Clin. Oral Implants Res. 2001, 13:655-65). In the 1990s calcium silicate ceramics began being used for stimulating bone growth. They are regarded as potential bio active materials and their degradation products do not incite an inflammatory reaction. However, drawbacks exist with these materials that compromise their physical and biological properties including their a.) inability to combine the required mechanical properties with open porosity b.) poor mechanical strength making them unsuitable for load-bearing applications; and c.) poor chemical instability (high degradation rate) leading to a highly alkaline condition in the surrounding environment which is detrimental to cell viability and limits their long-term biological applications.

Whilst other more recent ceramics such as HAp, Bioverit®, Ceraverit® and other calcium silicates have been found to bond to living bone and meet wide clinical applications, i.e., good bioactivity, they cannot be used in highly loaded areas, such as the cortical bone found in, for example, legs, due to the relative brittleness of these materials. Thus the materials possess good bioactivity, but lack full biodegradability after implantation and their mechanical strength is compromised [Hench L. L., J Am Ceram. Soc. 1998 81: 1705-28]. They are too brittle and fracture frequently. For at least this reason such materials typically find their use limited to coatings on metallic implants.

Another known material is doped Hardystonite, as detailed in International Publication No. WO 2010/003191. Doped Hardystonite is a biocompatible ceramic material comprising Sr, Mg or Ba doped Hardystonite ($Ca_2ZnSi_2O_7$).

It is an object of the present invention to overcome or ameliorate at least one of the disadvantages of the above mentioned prior art, or to provide a useful alternative.

It is an object of an especially preferred form of the present invention to provide for a composite biocompatible ceramic material that may be useful for improving the long term stability of, for instance, an implantable medical device and/or an implantable drug delivery device comprising such a material.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Although the invention will be described with reference to specific examples it will be appreciated by those skilled in the art that the invention may be embodied in many other forms.

The skilled person will appreciate that the term "biocompatible" defines a two-way response, i.e., the body's response to the material and the material's response to the body. The biocompatibility of a medical device refers to the ability of the device to perform its intended function, with the desired degree of incorporation in the host, without eliciting any significant or long-term undesirable local or systemic effects in that host.

SUMMARY OF THE INVENTION

According to a first aspect, the present invention provides a composite biocompatible ceramic material comprising a first and a second phase, wherein said first phase is doped Hardystonite ($Ca_2ZnSi_2O_7$) and said second phase is a metal oxide belonging to the spinel group of minerals.

The first phase is doped Hardystonite ($Ca_2ZnSi_2O_7$), as detailed in Publication No. WO 2010/003191. The Hardystonite is doped with at least one of strontium, barium and/or magnesium. The second phase is a metal oxide belonging to the spinel group of minerals. The spinels are any of a class of minerals of general formula $A^{2+}B_2^{3+}O_4^{2-}$ which crystallise in the cubic/isometric crystal system, with the oxide anions arranged in a cubic close-packed lattice and the cations A and B occupying some or all of the octahedral and tetrahedral sites in the lattice. A and B can be divalent, trivalent, or tetravalent cations, including magnesium, zinc, iron, manganese, aluminium, chromium, titanium, and silicon. In preferred embodiments the metal oxide is Gahnite ($ZnAl_2O_4$); this is sometimes called "zinc spinel". However, in other embodiments the metal oxide is the generically-named "Spinel" ($MgAl_2O_4$), or Hercynite ($FeAl_2O_4$), or combinations thereof.

The material defined according to the first aspect of the invention embodies a synergistic biocompatibility between said first and said second phases that is greater than the biocompatibility of the first and second phases taken alone.

In a preferred embodiment, said first phase comprises a molecular formula $[(Sr_aBa_bMg_c)Ca_{[2.0-\Sigma(a, b, c)]}ZnSi_2O_7]$, wherein $\Sigma(a, b, c)$ is between 0.05 to 0.9; and wherein the second phase comprises a molecular formula $[(Mg_xZn_yFe_z)Al_2O_4]$, wherein $\Sigma(x, y, z)=1$.

In another preferred embodiment, said first phase is a strontium calcium zinc silicate of the formula $Sr_{0.1}Ca_{1.9}ZnSi_2O_7$.

In an embodiment, the weight percentage of said first phase is between about 70 and about 99%; the respective weight percentage of said second phase is between about 30 and about 1%.

In a preferred embodiment, the material is an implant grade or medical grade material. The material preferably forms a hydroxyapatite layer upon exposure to bodily fluids, thereby to enhance biocompatibility within a mammalian body.

In other preferred embodiments, the material has a porosity of said material is between about 20 and about 80%, has an average pore size of between about 20 and about 500 microns and/or has a compressive strength of between about 2 and about 15 MPa.

For convenience, in the following discussion the first phase is referred to as "phase A" or "Sr-HT" and the second phase referred to as "phase B" or "mineral oxide". It will be appreciated, however, that the ceramic material of the invention may or may not have actual separate discrete phases, and that the material may be a homogenous mixture of these "phases", or may be a heterogeneous system with separately identifiable components comprising each "phase". The material of the invention is a composite material comprising doped Hardystonite and a mineral oxide.

The weight percentage of phase A in a mixture of phases A and B can be as low as 70% and as high as 99%, thereby making the respective weight percentage of phase B from 30 to 1%. In particular the amount of phase A may be 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 wt %, and the (non-respective) amount of phase B may be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt %.

The percentage of mineral oxide (phase B) in the final material is depended on the percentage of the alumina added to the doped Hardystonite (phase A). To explain, using Gahnite as an example, alumina will react with strontium-doped Hardystonite at high temperature, and partial melting will occur. The Gahnite phase will form from the melt. It has been found that additional alumina cannot be added over a certain amount as the scaffold tends to "collapse" due to large scale melting. This effectively means that the maximum alumina addition is about 15 wt %, which provides about 20% Gahnite in the final material. However, it is conceivable that the system could be configured to obtain up to about 30% Gahnite.

In WO 2010/003191, a novel material, strontium calcium zinc silicate ($Sr_{0.1}Ca_{1.9}ZnSi_2O_7$) was obtained by combining Zn and Sr ions in the Ca—Si system by partly replacing Ca ions in Hardsytonite with Sr. The preferred material was made by a sol-gel method. The new material showed surprisingly enhanced biological properties which were unexpectedly better than that of related known materials. In the present invention, Sr-HT was combined with Gahnite and a surprising synergistic effect was provided by the combination. In other words, the new composite ceramic material displays properties greater than the sum of the individual components. The new composite ceramic material of the invention, which preferably comprises an 80/20 wt/wt mixture of Sr-HT and Gahnite, is not only biocompatible, but it is clearly a superior material than commercially-available materials or the Sr-HT alone. The new composite ceramic material, Sr-HT/Gahnite (80/20 wt %), is also different to Sr-HT in composition and crystal structure and is superior to Sr-HT in at least one or more of the following parameters: composition; crystal structure; stability; mechanical strength (100 times better than commercially-available materials) and modulus of elasticity; hydrophilicity; fracture resistance; biological behaviour, e.g., attachment, spreading and induction of human osteoblast differentiation (osteoblast=bone forming cells).

It has been discovered that, surprisingly, a Sr-HT and Gahnite composite ceramic material displays enhanced biocompatibility and bioactivity as indicated by its osteoconductive and osteoinductive properties. Moreover, the Sr-HT and Gahnite composite ceramic material is particularly suited for the regeneration of bone and other tissue. In one embodiment, the composite biocompatible ceramic material of the invention finds particular utility in resurfacing arthritic joints to promote the growth of articular cartilage. In other embodiments, the composite biocompatible ceramic material of the invention is useful in the development of 3D scaffolds which promote migration, proliferation and differentiation of bone and endothelial cells, for example in orthopaedic and maxillofacial surgeries, and yet provides sufficient mechanical properties for load-bearing parts. The biocompatible ceramic material of the invention supports bone tissue regeneration/formation and vascularisation and yet also provides minimal fibrotic reactions. In one form, the present invention provides composite ceramic scaffolds for osteochondral defects. In other forms, the present invention provides a material which is coatable on currently used orthopaedic and dental implants to provide enhanced long-term implant stability. The composite ceramic biocompatible ceramic material of the invention is also useful as a coating for skeletal tissue regeneration. The present invention also finds use in cosmetic purposes over and above reconstruction and repair purposes, e.g., use of the material for nose and chin enhancement, as well as leg lengthening. The present invention finds particular relevance, however, for maxillofacial reconstruction applications, coatings for orthopaedic metal implants and dental applications.

In a preferred embodiment, the material is coated with at least one resorbable polymer material, selected from polyglycolides, polydioxanones, polyhydroxyalkanoates, polylactides, alginates, collagens, chitosans, polyalkylene oxalate, polyanhydrides, poly(glycolide-co-trimethylene carbonate), polyesteramides, and/or polydepsipeptides.

The skilled person will appreciate that the composition of Sr-HT/Gahnite cannot be simply described or predicted as a mixture of its precursors (Sr-HT and alumina) due to chemical reaction between alumina and HT during sintering to produce the Gahnite phase within the microstructure of the scaffold. Similarly, the mechanical properties and the bioactivity cannot be unambiguously predicted based on the precursors used, due to this chemical reaction. In addition, alumina is known to be biologically inert (i.e., not bioactive) and thus its use as a precursor for a bioactive ceramic is counterintuitive. It is surprising that Gahnite can be produced in situ to produce a coherent biocompatible ceramic material, whereas the simple mixing of Sr-HT with Gahnite will produce a less uniform material.

Without wishing to be bound by theory, it is believed that the addition of a relatively minor proportion of Gahnite into a Sr-HT material improves the mechanical properties due to two main factors: partial melting and formation of a glass phase between Sr-HT grains; and the presence of submicron Gahnite phase in the glass phase and the creation of a strong glass-ceramic phase which behaves like a strong "restraint" around the Sr-HT grains.

According to a second aspect, the present invention provides a composite biocompatible ceramic material comprising a first and a second phase, wherein said first phase comprises calcium zinc silicate doped with an element selected from the group of dopants consisting of Sr, Mg, Ba or a combination thereof; and the second phase comprises a metal aluminium oxide, wherein the metal is chosen from Mg, Zn, Fe or a combination thereof.

In relation to the first phase, preferably the dopant, namely the Sr, Mg, Ba or combination thereof at least partially substitutes the calcium in the calcium zinc silicate. In other preferred embodiments, wherein the dopant is Sr, the molecular formula of the Sr-calcium zinc silicate is [Sr, $Ca_{(2-x)}$ $ZnSi_2O_7$], wherein x is between 0.05 to 0.9. Preferably x=0.1, i.e., said first phase comprises the molecular formula [$Sr_{0.1}Ca_{1.9}ZnSi_2O_7$]. In one preferred embodiment, the calcium is at least partially substituted with Mg, or may be completely replaced by Mg.

In a preferred embodiment, the second phase is Gahnite ($ZnAl_2O_4$). Another preferred form of the invention comprises strontium calcium zinc silicate of the approximate molecular formula $Sr_{0.1}Ca_{1.9}ZnSi_2O_7$ and Gahnite.

Desirably, the strontium calcium zinc silicate material comprises a transmission X-ray diffraction pattern having the following diffraction angles 2-theta with three characteristic peaks: lines of "strong" intensity: 31.44 degrees; lines of "medium" intensity: 29.225 degrees, and line of third-strongest intensity: 36.565 degrees. Preferably, the strontium calcium zinc silicate material of one embodiment of the invention comprises a transmission X-ray diffraction pattern as per FIG. 1A of International Publication No. WO 2010/003191.

Preferably, the composite biocompatible ceramic material of the invention is biocompatible when placed in physiological fluid. Preferably, the biocompatible material of the invention forms a hydroxyapatite layer upon exposure to bodily fluids. As the skilled person will appreciate, the formation of hydroxyapatite is widely recognised as strong evidence that the body accepts the material as sui generis and is a requirement for the implant to chemically bond with living bone.

In relation to phase A, preferably the Sr:Ca ratio is between about 0.025 to 0.85. For example the Sr:Ca ratio may have a value of 0.025, 0.05, 0.075, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825 or 0.85. Of course, ratios in between these quoted examples are also permissible.

Preferably the molecular formula of the Sr-calcium zinc silicate is $Sr_xCa_{(2-x)}ZnSi_2O_7$, wherein x lies between 0.05 to 0.9. Preferably x=0.1. Alternatively, x may be 0.05, 0.15, 0.2, 0.25, 0.3, 0.35, 0.4, 0.45, 0.5, 0.55, 0.6, 0.65, 0.7, 0.75, 0.8, 0.85, 0.9, or anything in between the quoted numbers. It will be appreciated that the Sr dopant may alternatively be Mg or Ba. The dopant may also be a mixture of Sr, Mg, or Ba. In some embodiments, the strontium may be substantially substituted with a variant, which may be selected from the group consisting of Mg and Ba.

As discussed previously, the development of bioglass, glass-ceramics, and bioceramics containing CaO and $SiO_2$ for bone tissue regeneration has received great attention in the past three decades. The stimulatory effect of the Ca- and Si-containing ionic products released from materials on osteoblast proliferation, differentiation, and related gene expression, and mineralisation have also been well documented (see, for example, Xynos I. D., et al in Ionic products of bioactive glass dissolution increase proliferation of human osteoblasts and induce insulin-like growth factor II mRNA expression and protein synthesis, Biochem. Biophy. Res. Commun. 2000; 276:461-465). $CaSiO_3$-based materials are considered potential bioactive materials for bone tissue regeneration and implant coatings due to their bioactivity. However, a major drawback of the $CaSiO_3$ ceramics is their relatively high dissolution rate leading to a high alkaline pH value in the surrounding environment (see, for example Siriphannon P., et al in Formation of hydroxyapatite on $CaSiO_3$ powders in simulated body fluid, J. Eur. Ceram. Soc. 2002; 22:511-520). Indeed, the bonding of $CaSiO_3$ coatings to a titanium substrate degrades with the increasing immersion time in simulated body fluid (SBF) due to the relatively fast dissolution rate of the coating, which limits further biological applications. The present Inventors have unexpectedly found that the composite ceramic biocompatible ceramic material of the invention provides a bioceramic with significantly improved properties compared to previously known calcium silicates and previously known bioceramic materials. In particular, in certain embodiments the composite biocompatible ceramic material of the invention provide many of the advantages of the $CaSiO_3$ materials, but ameliorate many of its known disadvantages. The composite biocompatible ceramic material of the invention displays a relatively reduced dissolution profile, which is associated with a relatively reduced pH compared with $CaSiO_3$ materials. Further, the densification of the calcium silicate is stimulated and the ability of apatite formation is maintained. It is also likely that Human Bone Derived Cell proliferation is stimulated.

Further, in certain embodiments, the composite ceramic biocompatible material of the invention exhibits superior mechanical properties such as bending strength and fracture toughness. It may also allow attachment and proliferation of bone cells. In particular, in certain embodiments, the composite biocompatible ceramic material of the invention has been found to form a chemical bond with bone, and the ability to form an apatite layer. Furthermore, the composite biocompatible ceramic material of the invention displays relatively reduced corrosion as compared with $CaSiO_3$.

According to a third aspect, the present invention provides a method for the preparation of a composite biocompatible ceramic material, said method comprising the steps of: providing a sol of precursor materials for producing a calcium zinc silicate doped with an element selected from the group consisting of Sr, Mg, Ba or combinations thereof, and at least partially gelling the sol into a first sol; providing a sol of precursor materials for producing Gahnite, and at least partially gelling the sol into a second sol; mixing the first and second sols; and drying and sintering the mixed and dried sols to thereby form the composite biocompatible ceramic material.

According to a fourth aspect, the present invention provides a method for the preparation of a composite biocompatible ceramic material, said method comprising the steps of: producing a strontium-doped calcium zinc silicate powder by a sol-gel method; mixing and mechanically activating said strontium-doped calcium zinc silicate powder with alumina powder by a rotary ball mill machine; and drying and sintering the powder obtained to form said composite biocompatible ceramic material. Preferably the mixing and mechanical activation is by rotary ball mill machine and conducted for one week.

The particles of starting materials are milled in a rotary milling machine, which promotes diffusion and reactivity between alumina and Sr-HT particles. During milling, the particles will break into smaller pieces and their surface area increases, which in turn enhances diffusion at high temperatures. Moreover, the distribution of alumina powder between Sr-HT powder will be more uniform and homogenous. Whilst the mechanism for formation of Gahnite from the mixing of alumina and Sr-HT phase is unclear, without wishing to be bound by theory the Inventors hypothesise that alumina may react with Sr-HT, leading to the partial melting of some particles in the surface of Sr-HT. Then, during the cooling down stage, some crystals of Gahnite ($ZnAl_2O_4$) may crystallise from the melt containing the Al, O, Zn, Ca and Si elements, and unreacted elements will form a glass phase.

The composite biocompatible ceramic material according to the third and fourth aspects is sol-gel derived. However, it will be appreciated that in other embodiments any method of synthetic production of the composite biocompatible ceramic material of the invention would fall within the purview of the present invention. For example, in another embodiment, the starting materials are melted, cooled and the resulting material pulverised. The resulting powder can then be formed and hot-pressed, as is well known in the art.

According to a fifth aspect, the present invention provides a composite biocompatible ceramic material when produced by a method according to the third or fourth aspects of the invention.

According to a sixth aspect the present invention provides a composition for the preparation of a composite biocompatible ceramic material, the composition comprising alumina and a Sr-doped calcium zinc silicate in the form of strontium-doped Hardystonite $[Sr_xCa_{(2-x)}ZnSi_2O_7]$, wherein x is between about 0.05 and about 0.9.

According to a seventh aspect the present invention provides an implantable medical device comprising a composite biocompatible ceramic material defined according to the first, second or fifth aspects of the invention.

The medical device is preferably chosen from the group consisting of: a 3D implantable scaffold, an orthopaedic implant for reconstructive surgery, a dental implant/prostheses, a spine implant, implants for craniofacial reconstruction and alveolar ridge augmentation, for cartilage regeneration, an osteochondral defect implant, a surgical fastener (such as a clamp, clip, sheath, or staple), a surgical fabric, an artificial heart valve (such as a sheath, flange, leaf or hinge), a strut, a stent or a stent-graft, biphasic scaffolds for osteochondral defect, scaffolds for bone tissue regeneration and maxillofacial reconstruction that promote vascularisation and bone tissue ingrowth, coating on currently used orthopaedic and dental implants, thereby improving long-term implant stability and devices for drug delivery. However, it will be appreciated that there are many other devices which would be within the scope of the present invention. In other embodiments, the composite biocompatible ceramic material of the invention may be formed into a surgical device or as a coating on a surgical device. Also within the scope of the present invention is, for instance, a bone implant, a tooth filling, or a biocement comprising the composite biocompatible ceramic material defined according to the invention.

In one embodiment, the medical device is permanently implanted. However, in other embodiments the medical device may be temporarily implanted. In some aspects the medical device may be substantially biodegradable or resorbable.

In one embodiment, the porosity of the medical device comprising the composite biocompatible ceramic material of the invention is between about 20 to about 80%. However, it will be appreciated that the device could be formulated or produced to have lower or greater porosity according to the intended or desired use, and any porosity range would be within the purview of the present invention. For example, porosities of 50, 55, 60, 65, 70, 75, 80, 85, 90 or 95%—or anything in between these exemplary numbers are possible.

In one embodiment, the pore size of the device is between about 20 to about 500 µm (microns). However, it will be appreciated that the device could be formulated or produced to have lower or greater pore size according to the intended or desired use, and any pore size would be within the purview of the present invention. For example, pore sizes of 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 microns are possible, as are any pore sizes in between any one of these quoted exemplary numbers.

Implantable devices according to the present invention have many properties that make them suitable for use as implants, including high mechanical strength, resistance to fatigue, corrosion resistance, and biocompatibility. The implants may be implanted in animals, non-limiting examples of which include reptiles, birds, and mammals, with humans being particularly preferred. Preferably, the compressive strength of said implantable devices is between about 2 to 15 MPa.

The devices of this invention may be implanted into a body in different ways, including, but not limited to subcutaneous implantation, implantation at the surface of the skin, implantation in the oral cavity and other surgical implantation methods.

In one embodiment, the composite biocompatible ceramic material of the present invention may be coated with at least one resorbable polymer material, non-limiting examples of which include polyglycolides, polydioxanones, polyhydroxyalkanoates, polylactides, alginates, collagens, chitosans, polyalkylene oxalate, polyanhydrides, poly(glycolide-co-trimethylene carbonate), polyesteramides, and/or polydepsipeptides.

Alternatively, the coating material may comprise healing promoters such as thrombosis inhibitors, fibrinolytic agents, vasodilator substances, anti-inflammatory agents, cell proliferation inhibitors, and inhibitors of matrix elaboration or expression; examples of such substances are provided in U.S. Pat. No. 6,162,537, to Solutia Inc. The present invention also contemplates using a polymer coating, (e.g., a resorbable polymer) in conjunction with a healing promoter to coat the implantable medical device.

The implantable medical device may be resorbable or completely inert towards biodegradation. When the device is resorbable, the in vivo degradation leaves behind a scaffold that reinforces the injured tissue.

According to an eighth aspect the present invention provides a bone implant, a tooth filling, or a biocement comprising a composite biocompatible ceramic material defined according to the first, second or fifth aspects of the invention.

According to a ninth aspect of the present invention there is provided a method for producing an implantable medical device, said method comprising the steps of: transferring or applying a composite biocompatible ceramic material defined according to the first, second or fifth aspects of the invention to a substrate, thereby forming said implantable medical device.

It will be appreciated that there are a number of methods of applying a biocompatible material to a supporting surface or substrate, and any of these methods fall within the scope of the present invention. For example, in one embodiment, the material is plasma spray coated. As is well known in the art, this method essentially comprises the steps of spraying molten or heat-softened material onto a surface to provide the coating. The material, in the form of powder, is injected into a high temperature plasma flame, where it is rapidly heated and accelerated to a high velocity. The hot material impacts on the substrate surface and rapidly cools thereby forming a coating. The coatings possess a dense structure with a thickness of about 50 μm (microns) and the bonding strength is higher than hydroxyapatite coatings.

According to a tenth aspect of the present invention there is provided an implantable drug delivery device comprising a composite biocompatible ceramic material defined according to the first, second or fifth aspects of the invention. It will be appreciated that the drug delivery device can be configured deliver any drug or combination of drugs and can be shaped to suit the particular application.

According to an eleventh aspect, the present invention provides a method for improving the long-term stability of an implantable medical device, said method comprising the step of coating said device with a composite biocompatible ceramic material defined according to the first, second or fifth aspects of the invention.

Preferably, the coating further includes a biocompatible polymer, which in one embodiment is polylactid glycolic acid (PLGA). In one form, the implantable medical device is a biphasic scaffold for an osteochondral defect.

According to a twelfth aspect of the present invention there is provided use of a composite biocompatible ceramic material defined according to the first, second or fifth aspects of the invention for the regeneration or resurfacing of tissue, said use comprising contacting said tissue with a quantity of said material for a sufficient period to at least partially effect said regeneration or resurfacing.

In an embodiment, the composite biocompatible ceramic material of the invention contacted with tissue includes an S100A8 or a S100A9 polypeptide, or a polynucleotide encoding S100A8 or S100A9 operably linked to a promoter, as disclosed in International Publication No. WO 2006/047820, or any other protein that is shown to be important in bone and cartilage regeneration.

According to a thirteenth aspect of the present invention there is provided a method for regenerating or resurfacing tissue, said method comprising contacting said tissue with a quantity of a composite biocompatible ceramic material defined according to the first, second or fifth aspects of the invention for a sufficient period to at least partially effect said regeneration or resurfacing.

In an embodiment, the composite biocompatible ceramic material of the invention contacted with tissue includes an S100A8 or a S100A9 polypeptide, or a polynucleotide encoding S100A8 or S100A9 operably linked to a promoter, as disclosed in International Publication No. WO 2006/047820, or any other protein that is shown to be important in bone and cartilage regeneration.

According to a fourteenth aspect of the present invention there is provided use of a composite biocompatible ceramic material defined according to the first, second or fifth aspects of the invention for forming osseous tissue on an orthopaedic defect upon contacting said defect with said material for a predetermined period.

According to a fifteenth aspect of the present invention there is provided a method for forming osseous tissue on an orthopaedic defect, said method comprising contacting said defect with a composite biocompatible ceramic material defined according to the first, second or fifth aspects of the invention for a predetermined period.

According to a sixteenth aspect of the present invention there is provided use of a composite biocompatible ceramic material defined according to the first, second or fifth aspects of the invention for treating orthopaedic conditions by contacting a relevant area of a patient in need of such treatment with an effective regenerating amount of said material.

According to a seventeenth aspect of the present invention there is provided a method for treating orthopaedic conditions, said method comprising contacting a relevant area of a patient in need of such treatment with an effective regenerating amount of a biocompatible composition comprising a composite biocompatible ceramic material defined according to the first, second or fifth aspects of the invention.

According to an eighteenth aspect of the present invention there is provided a kit for regenerating or resurfacing tissue, said kit comprising, a composite biocompatible ceramic material defined according to the first, second or fifth aspects of the invention; a therapeutic agent which stimulates and accelerates tissue regeneration; and instructions for the sequential or simultaneous administration of said material and said agent.

According to a nineteenth aspect of the present invention there is provided use of a composite biocompatible ceramic material defined according to the first, second or fifth aspects of the invention in a liquid injectable formulation for regenerating or resurfacing tissue. The material of the invention is preferably dispersed, suspended or dissolved in a suitable carrier. The injectable dispersion/suspension/solution is then injected at or proximal to the target site within a patient. Suitable carrier/s and injection techniques are well within the knowledge and ability of one appropriately skilled in the art.

According to a twentieth aspect of the present invention there is provided a method for regenerating or resurfacing tissue, said method comprising administering to a patient in need to such treatment a liquid injectable formulation comprising an effective amount of a composite biocompatible ceramic material defined according to the first, second or fifth aspects of the invention.

The composite biocompatible ceramic material according to the invention may be used as a fully synthetic bone graft substitute. Due to its interconnected pores, the material serves as an ideal osteoconductive scaffold and supports the formation of new host bone. The present invention provides, in one or more embodiments, one or more of the following advantages: optimised porosity; improved mechanical strength and elasticity; enhanced bone ingrowth and vascularisation; avoids potential problems common in grafting methods; is formable to almost any shape to suit the application; easy to use; combines with autologous bone marrow or blood; and/or displays accelerated and enhanced osteointegration The uses of the present invention are manifold. In one or more embodiments it may be useful for: bone void fillings or augmentation in zones requiring cancellous rather than cortical bone; filling of bone defects after trauma, reconstruction, or correction in non-load or load-bearing indications; trauma and orthopaedics; filling of voids caused by cysts or osteotomies, filling of defects arising from impacted fractures, refilling of cancellous bone-harvesting sites, arthrodesis and non-unions; spine surgery: Postero-lateral fusion, interbody fusion (as cage-filling material), vertebrectomies (as filling material of the vertebral implants), refilling of bone graft-harvesting sites, or cranio-maxillofacial surgery: Reconstruction of mandibular defects and sinus lifts.

BRIEF DESCRIPTION OF THE FIGURES

Preferred embodiments of the invention will now be described, by way of example only, with reference to the accompanying figures in which:

FIG. 3, part "B" shows X-ray diffraction pattern of a Sr-HT-20% Gahnite scaffold;

FIG. 3, part "C" shows line mapping of the elements via the designated path at the surface of the scaffolds passing the three constituents;

FIG. 5 shows the concentration of ions (Ca, Si, Zn, Sr and Al) released from Sr-HT-20% Gahnite scaffold and the related pH of simulated body fluid at increasing soaking times. Note that it can be seen that dissolution was gradual with no significant change in pH, minimal loss of weight and release of ions, reflecting the stability of the newly developed scaffolds;

FIG. 13 shows scaffolds implanted in the rabbit radial load-bearing critical size defect.

DEFINITIONS

Figure 1:
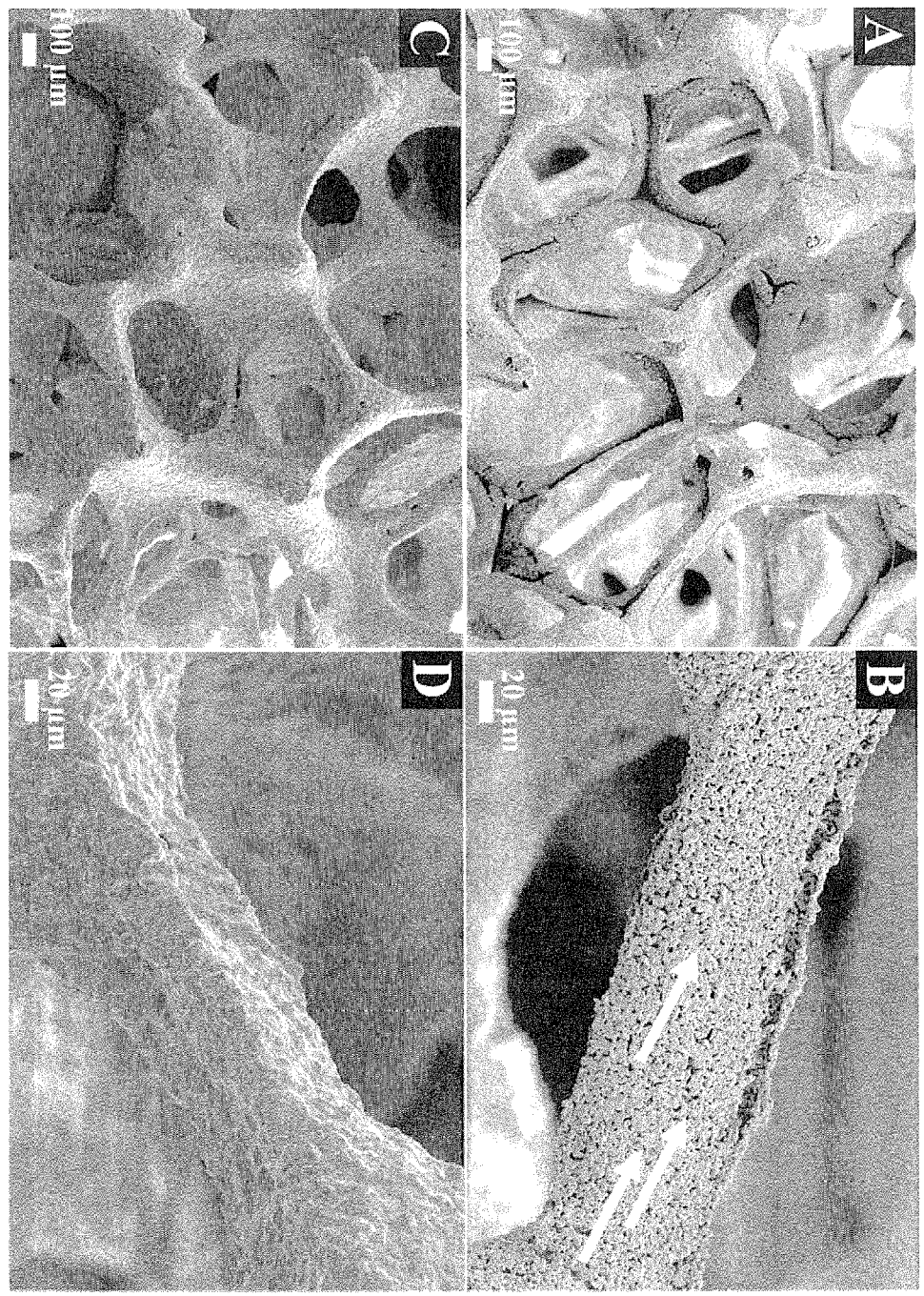
FIGS. 1A to D are micrographs showing the macrostructure and microstructure of Sr-HT (A, B) and Sr-HT-20% Gahnite (C, D) scaffolds indicating a crack- and defect-free structure of the Sr-HT-20% Gahnite scaffold, compared to a cracked Sr-HT scaffold (arrows)

In describing and claiming the present invention, the following terminology will be used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

The recitation of a numerical range using endpoints includes all numbers subsumed within that range (i.e., "1 to 5" includes, e.g., 1, 1.5, 2, 2.75, 3, 3.80, 4, 4.1685, 5, etc.).

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, an "implant" refers to an article or device that is placed entirely or partially into an animal, for example by a surgical procedure. The animal may be a human, a horse, a cow, pig, sheep, etc.

Other than in the operating examples, or where otherwise indicated, all numbers expressing quantities of ingredients or reaction conditions used herein are to be understood as modified in all instances by the term "about". The examples are not intended to limit the scope of the invention. In what follows, or where otherwise indicated, "%" will mean "weight %", "ratio" will mean "weight ratio" and "parts" will mean "weight parts". However, it will be appreciated that features usually expressed in terms of percentage alone, e.g., porosity, will not be subject to this definition.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

As used herein, "HT" refers to calcium zinc silicate ($Ca_2ZnSi_2O_7$), and "Sr-HT" refers to a calcium zinc silicate scaffold doped with strontium, e.g., $Sr_{0.1}Ca_{1.9}ZnSi_2O_7$. "TCP" refers to tricalcium phosphate. "HA" denotes hydroxyapatite.

Preferred Embodiment of the Invention

Preferred embodiments of the present invention will be described in the following passages.

A new ceramic material has been developed which can be manufactured into porous scaffolds for use in, for example, bone regeneration. The material contains two phases: one is strontium-doped calcium zinc silicate (Sr—$Ca_2O_7Si_2Zn$) and the other is Gahnite ($ZnAl_2O_4$). The Gahnite phase is approximately 20% and Sr-(calcium silicate zinc) is approximately 80% by weight. The ceramic powder is preferably prepared by combining the sol-gel and mechanical activation methods, as disclosed in the priority application, AU 2011902160.

This composite ceramic material in the form of scaffolds displayed a porosity of ~85% and pore interconnectivity of ~100% (thereby reproducing cancellous bone architecture), was prepared and characterised as follows:

Firstly, Sr-HT powder was prepared by the sol-gel method. Alumina powder and Sr-HT powder were then mixed together and activated by rotary ball milling for four days. The ceramic slurry was prepared by mixing the obtained powder and a polyvinyl alcohol solution. Polymer foam templates were coated by being dipped into the ceramic slurry and then dried over night in an oven at 37° C. The dried powder coated foam templates were sintered in an electric furnace at 1250° C. for 3 h which removed the polymer template and densified the powder.

Turning now to the accompanying Figures, FIG. 1 shows microstructural analysis of struts and pore morphology by field emission electron microscopy. FIG. 1 clearly shows crack- and defect-free structure of the Sr-HT:Gahnite biocompatible material (20 wt % Gahnite) compared to the weak and relatively high level of cracks contained in Sr-HT scaffolds. The arrows show numerous cracks and pores resulting from the poor sintering ability of the scaffold characteristic for the scaffold preparation method. However these defects were eliminated in Sr-HT/20 wt % Gahnite through partial melting.

Figure 2:
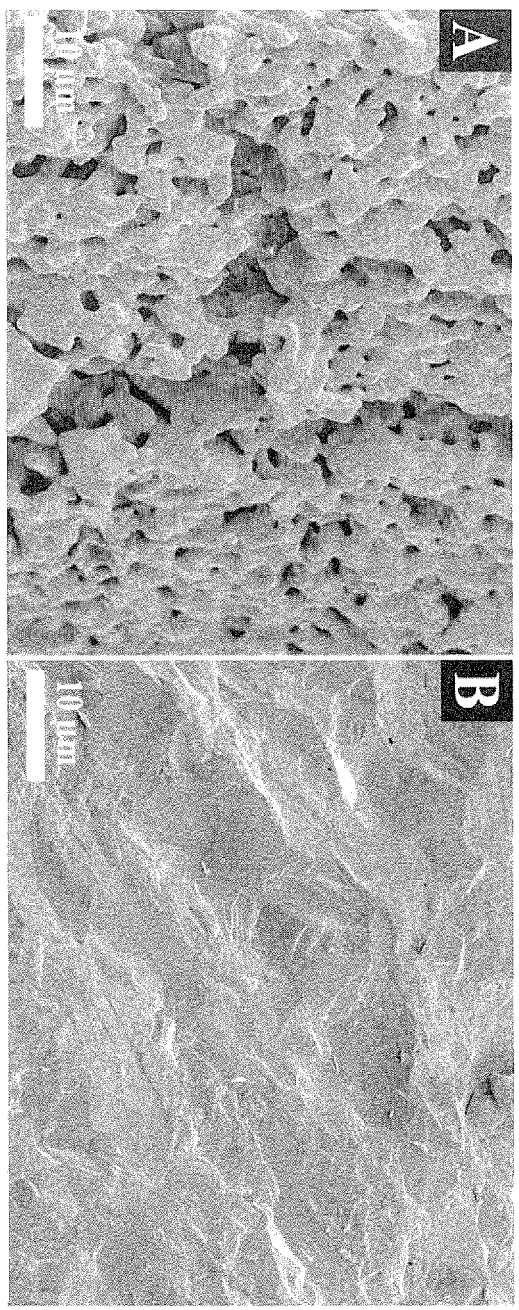
FIG. 2 shows the fracture surface of Sr-HT (A) and Sr-HT-20% Gahnite (B) scaffolds indicating different fracture mechanisms for each (the Sr-HT scaffold crack has propagated through the micro-pores and caused a catastrophic breakage, while the cleavage in the Sr-HT-20% Gahnite scaffold was by propagating through the grains, a process requiring high energy)

FIG. 2 shows fractography of the broken surfaces of the Sr-HT:Gahnite biocompatible material (20 wt % Gahnite) scaffold by FE-SEM, showing different fracture mechanisms compared to a pure Sr-HT scaffold. To explain, for the Sr-HT scaffold the crack has propagated through the micropores and caused a catastrophic breakage. In contrast, for the Sr-HT: Gahnite biocompatible material (20 wt % Gahnite), cleavage has been through rupturing the grains, which requires a very high plastic deformation energy.

Figure 3:
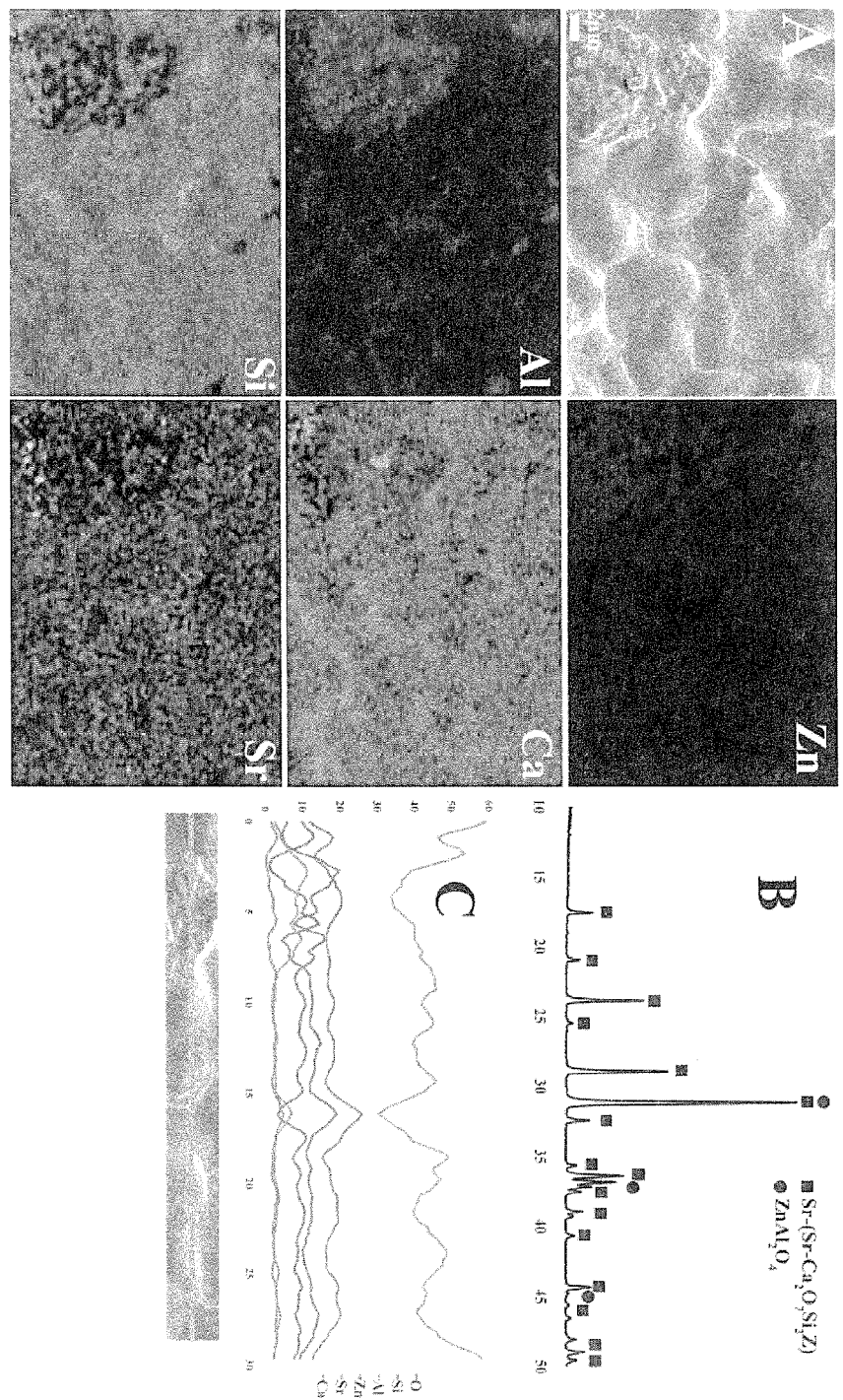
FIG. 3, part "A" shows elemental mapping of a typical microstructure of Sr-HT-20% Gahnite scaffold comprising three constituents; (i) grains, (ii) glass phase and (iii) crystalline precipitates.

FIG. 3A shows microstructure phase analysis by elemental mapping. X-ray pattern of Sr-HT/20 wt % Gahnite as shown in FIG. 3B scaffolds depict the presence of two phases of Sr-HT and Gahnite. FE-SEM showed Sr-HT:Gahnite biocompatible material (20 wt % Gahnite) consisted of three components; (i) grains, (ii) glass phase and (iii) crystalline precipitates. The grains belong to the Sr-HT phase, and submicron crystals are Gahnite ($ZnAl_2O_4$) which is confirmed by elemental analysis showing the high concentration of Al and Zn. Glass phases in grain boundaries and around Sr-HT grains are characterised by high concentrations of oxygen, aluminium and strontium.

Figure 4A:
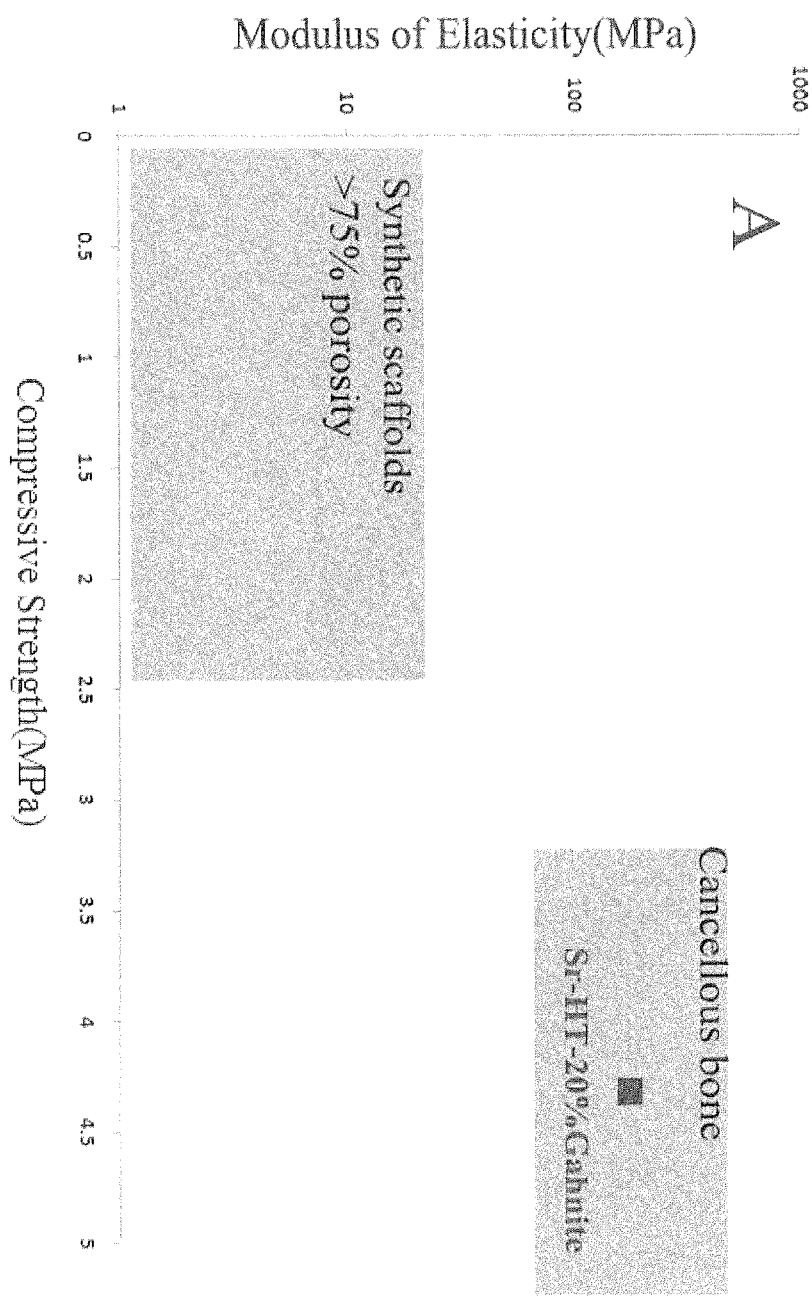
FIG. 4A shows mechanical properties of the Sr-HT-20% Gahnite scaffold compared to all the currently available synthetic scaffolds (regardless of the composition) with more than 75 percent porosity.
Figure 4B:
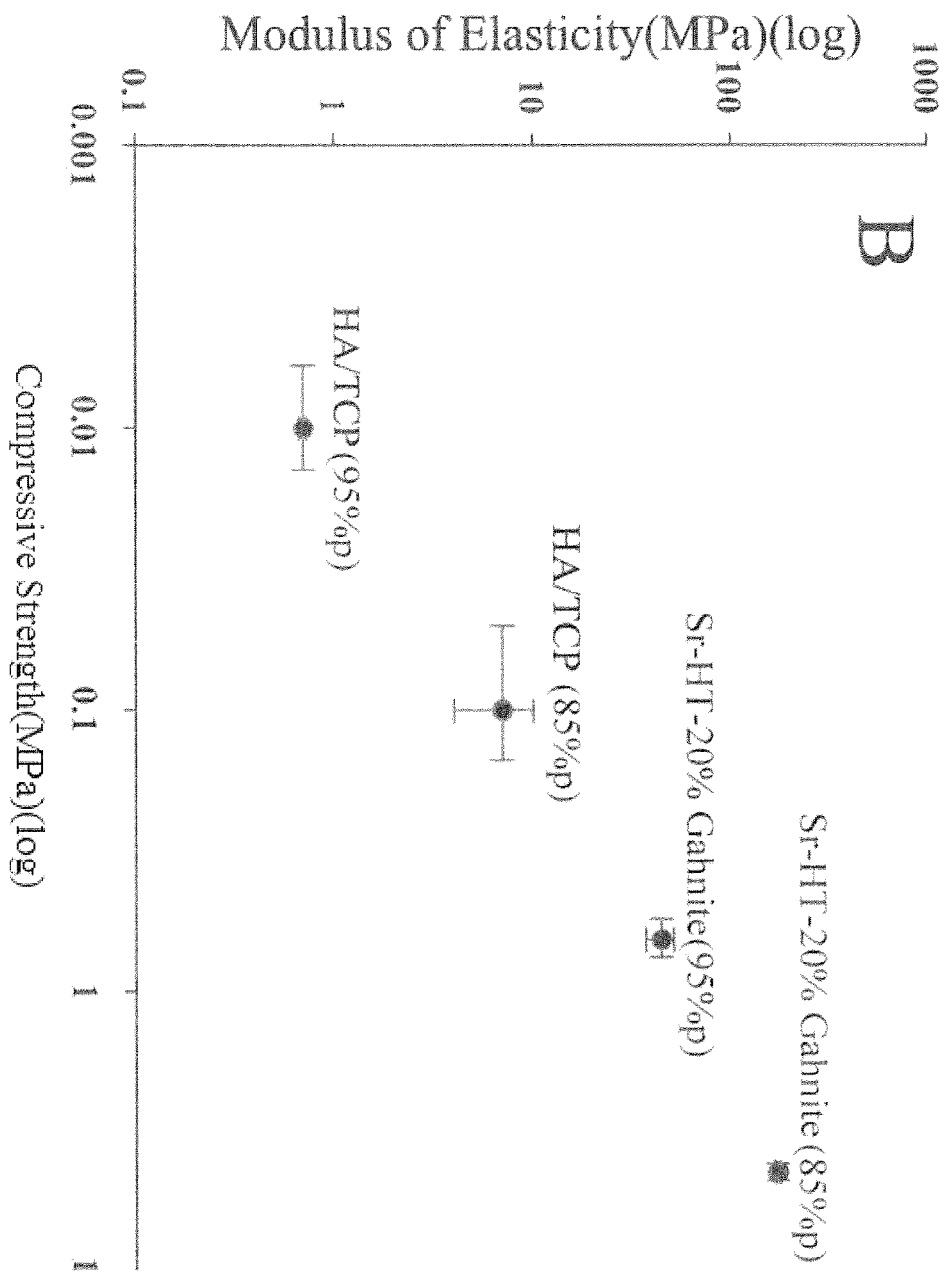
FIG. 4B shows comparison of the compressive strength and modulus of elasticity of Sr-HT-20% Gahnite scaffold with the commercial available HA/TCP scaffolds of different porosities (95% and 85%). Note that at each porosity the strength is approximately 100 times greater for the newly developed scaffolds compared to HA/TCP.
Figure 4C:
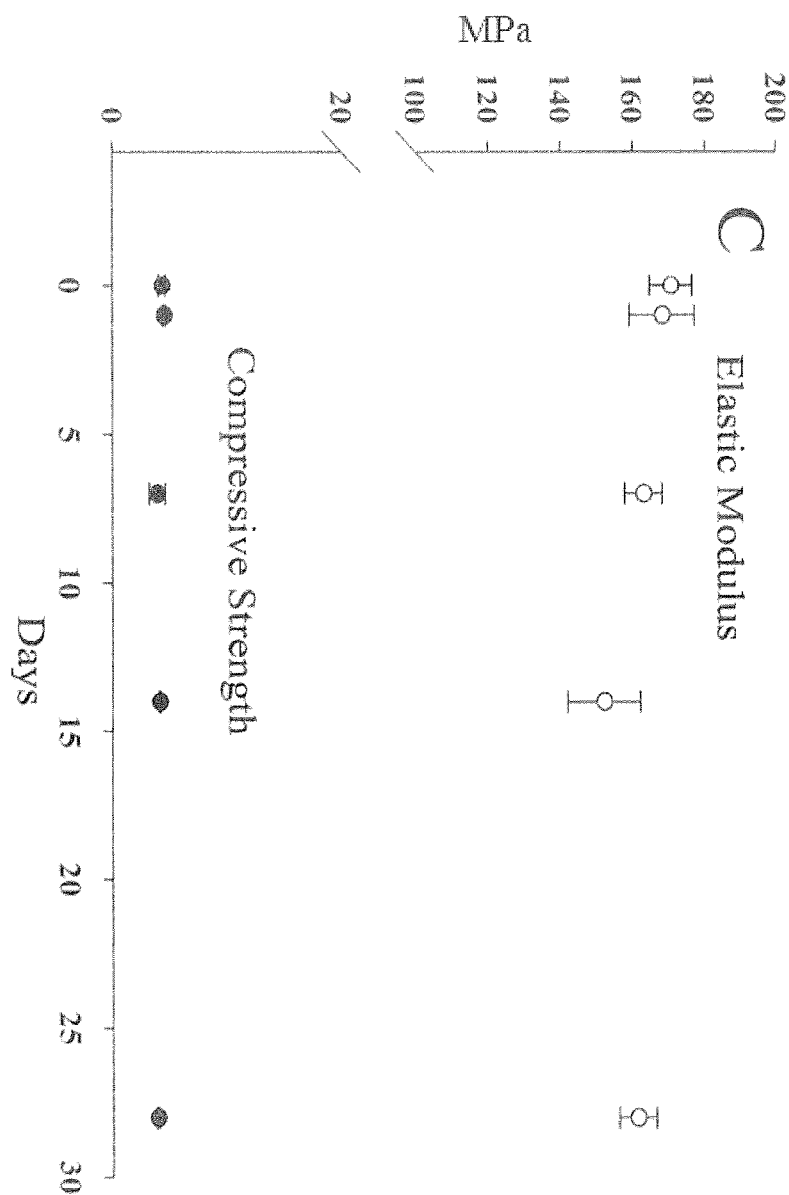
FIG. 4C shows the mechanical properties of the Sr-HT-20% Gahnite scaffolds after soaking in simulated body fluid for increasing periods of time showing no loss of mechanical properties with exposure to biological fluids.

FIG. 4 shows the mechanical properties (compressive strength and modulus of elasticity) of Sr-HT:Gahnite biocompatible material (20 wt % Gahnite) in wet and dry conditions up to 28 days. The dry compressive strength and modulus of elasticity of the manufactured scaffolds were ~4

MPa and ~170 MPa, respectively. These strengths are similar to the mechanical properties of cancellous bone and much higher than all of the bone scaffolds with more than 75% porosities, regardless of their composition.

The compressive strength of Sr-HT:Gahnite biocompatible (20 wt % Gahnite) scaffolds is 40 and 20 times more than that for HA/TCP and Sr-HT scaffolds respectively. The modulus of Sr-HT:Gahnite biocompatible (20 wt % Gahnite) scaffolds is 17 and 10 times more than that for HA/TCP and Sr-HT scaffolds.

It can be seen that even Sr-HT:Gahnite biocompatible (20 wt % Gahnite) scaffolds with 95% porosities have much higher compressive strength (~10 times) compared to commercially available HA/TCP scaffolds with 85% porosities, indicating that the composite ceramic materials of the invention are superior for load-bearing applications. Furthermore, the mechanical properties of the scaffolds of the invention remain nearly constant after 28 days soaking in a simulated body fluid solution.

FIG. 5 shows Al, Zn, Si, Ca and Sr ion release profiles after incubation in simulated body fluid. The results show a very mild degradation behaviour of Sr-HT:Gahnite biocompatible (20 wt % Gahnite) scaffolds and gradual ion release over time, indicating these ions would be able to potentially promote local bone growth and that these materials would be gradually resorbable.

Ink diffusion studies (see, FIG. 6) show that Sr-HT:Gahnite biocompatible (20 wt % Gahnite) scaffolds provide a better environment for ink infiltration of the inner regions of the scaffolds in all three directions. Blue coloration due to the ink diffusion and uptake by the surface of the scaffolds highlights the efficiency of using these scaffolds in biological applications that require the flux of fluids and cells within porous matrices.

Biological Data

Different groups of scaffolds were prepared for biological examinations;
1—HA/TCP
2—Sr-HT
3—Sr-HT-5% Gahnite
4—Sr-HT-11% Gahnite scaffold
5—Sr-HT-14% Gahnite scaffold
6—Sr-HT/Gahnite (20 wt %) scaffold Materials and Methods Isolation and Culture of Primary HOBs HOBs were isolated from normal human trabecular bone as previously described (Roohani-Esfahani S. I., Nouri-Khorasani S., Lu Z., Appleyard R., Zreiqat H., "The influence hydroxyapatite nanoparticle shape and size on the properties of biphasic calcium phosphate scaffolds coated with hydroxyapatite-PCL composites Biomaterials", 2010 July; 31(21):5498-509) Briefly, bone was divided into 1 mm$^3$ pieces, washed several times in phosphate buffered saline (PBS), and digested for 90 min at 37° C. with 0.02% (w/v) trypsin in PBS. Digested cells were cultured in complete media containing α-Minimal Essential Medium (α-MEM), supplemented with 10% (v/v) heat-inactivated fetal calf serum (FCS), 2 mM 1-glutamine, 25 mM Hepes Buffer, 2 mM sodium pyruvate, 30 mg/mL penicillin, 100 mg/mL streptomycin and 1 mM 1-ascorbic acid phosphate magnesium salt. The cells were cultured at 37° C. with 5% $CO_2$, and the medium refreshed every three days until confluence when cells were passaged.

Cell Attachment and Morphological Observation

After the cells reached 80-90% confluence, they were trypsinised using TrypLE™ Express, subsequently centrifuged and suspended in complete media to produce a cell suspension with a density of $11 \times 10^4$ cells per mL. Then, a 100 µL cell suspension was added into each scaffold placed in 24-well cell culture plate. After 1 h of incubation in a 37° C. incubator, a 1 mL cell culture medium was added into each well. For SEM observation, cells at 24 h were fixed in a 4% paraformaldehyde solution, post-fixed in 1% osmium tetroxide in PBS for 1 h, then dehydrated in a serial of graded ethanol solution (30, 50, 70, 90, 95, and 100%), and finally dried in hexamethyldisilizane for 3 min. The dried coating samples were gold-sputtered prior to scanning electron microscope (SEM) observation conducted using standard procedures.

Quantitative Real Time Polymerase Chain Reaction (qRT-PCR)

Total RNA was isolated from HOBs cultured on the scaffolds using Trizol reagent (Sigma) and RNeasy Mini Kit from Qiagen according to the manufacturer's instructions. First strand cDNA was synthesised from 0.7 µg total RNA using the Omniscript RT Kit according to the manufacturer's instructions. The cDNA was analyzed for the osteoblast-related genes Runx-2, and osteocalcin. Their relative gene expression levels were obtained by normalising to the housekeeping gene [Glyceraldehyde 3-phosphate dehydrogenase (GAPDH)]. The mRNA expression levels of Runx-2, osteocalcin and GAPDH were analyzed using quantitative real-time polymerase chain reaction (qRT-PCR).

Results—Cell Attachment

Figure 6:
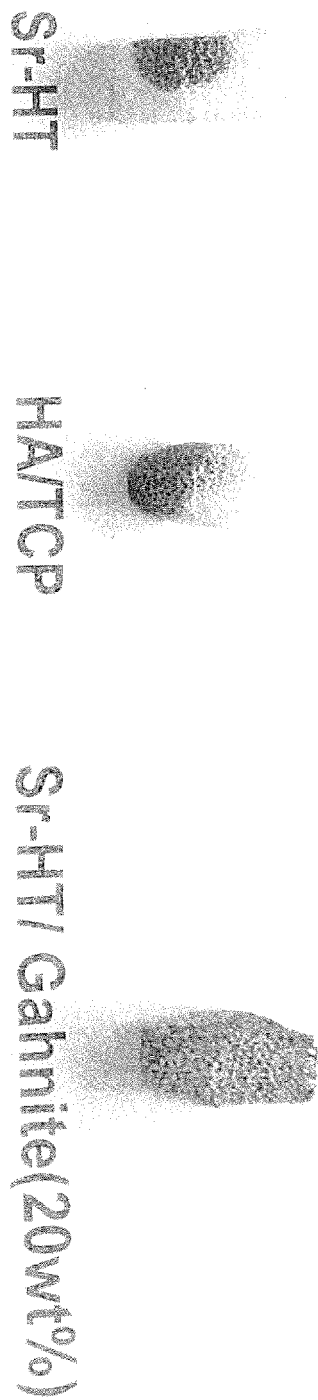
FIG. 6 shows images of (left-to-right, respectively) Sr-HT, HA/TCP and Sr-HT/Gahnite (20 wt %) scaffolds after diffusion studies using of toluidine blue ink. Note that Sr-HT/Gahnite (20 wt %) scaffolds induced significantly more extensive ink infiltration through the scaffolds than either Sr-HT or HA/TCP, reflecting the superiority and efficiency of using these scaffolds in biological applications that require the flux of fluids and cells within porous matrices.
Figure 7:
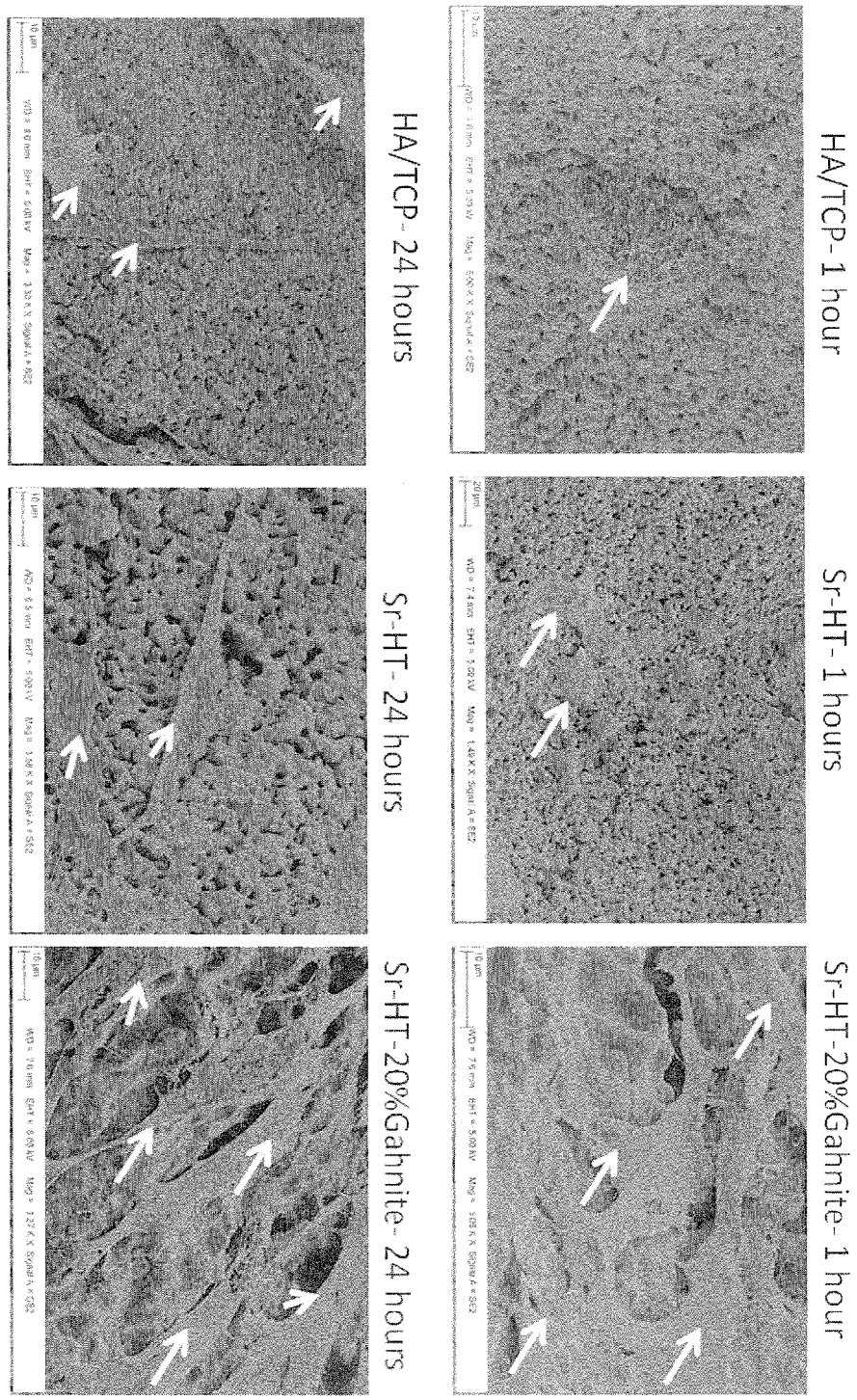
FIG. 7 shows primary human bone derived cells (HOB) attachment (arrows) to the HA/TCP, Sr-HT and Sr-HT/Gahnite (20 wt %) scaffolds after 1 and 24 hours of seeding.
Figure 8:
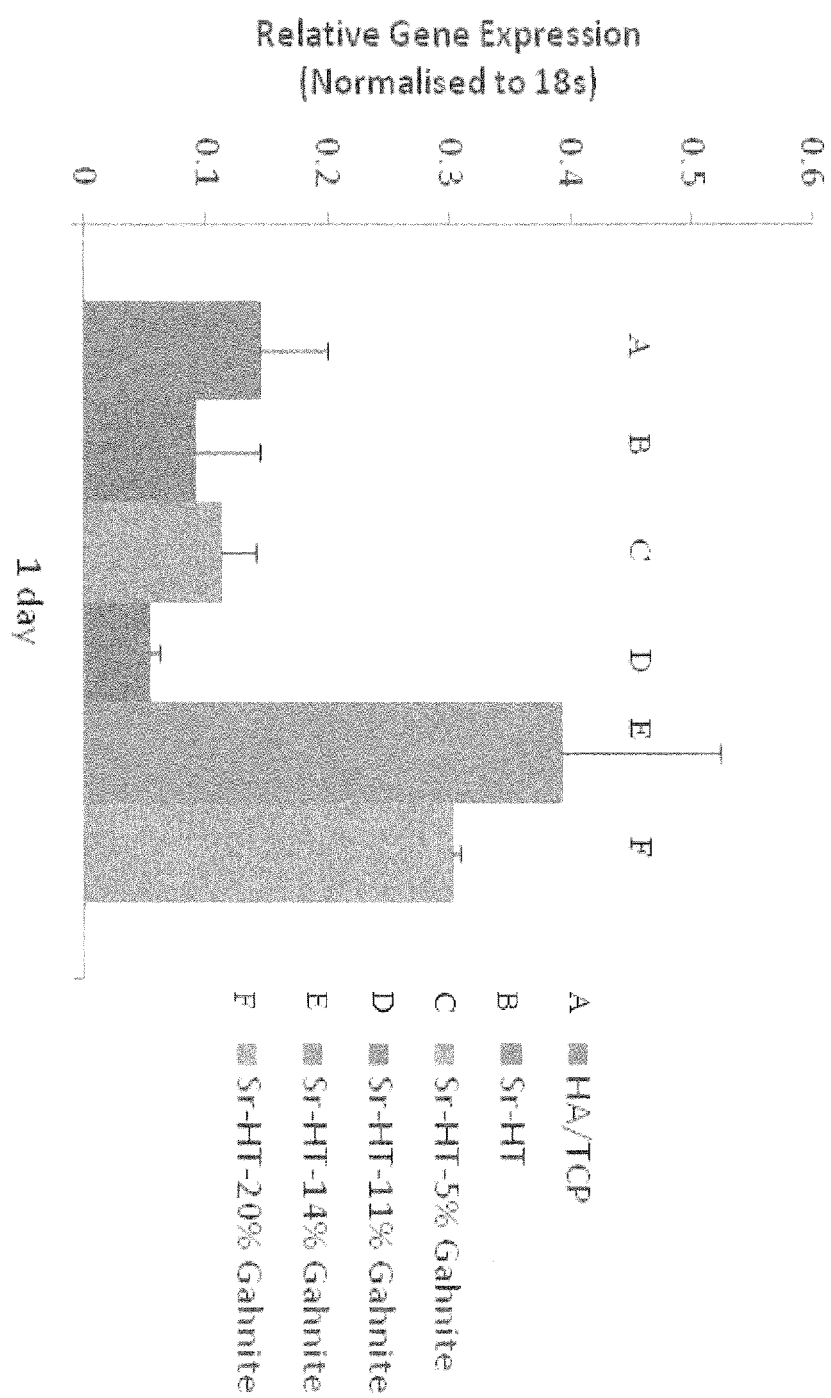
FIGS. 8 and 9 respectively show mRNA expression for Runx-2 and osteocalcin by HOB seeded on the various types of the scaffolds (with * p<0.05).
Figure 9:
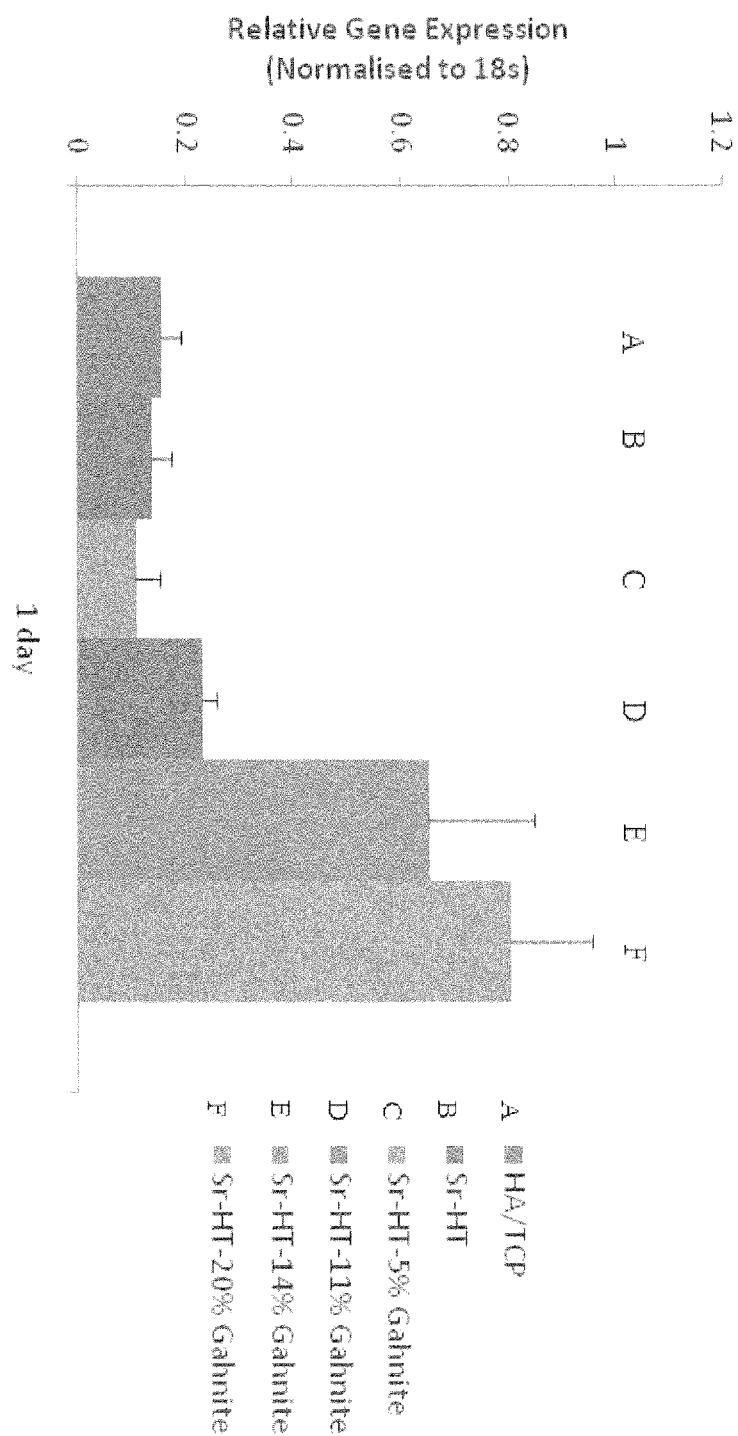

The typical morphology of the HOBs cultured on the Sr-HT/Gahnite (20 wt %), and compared to Sr-HT and to the commercially available hydroxyapatite/tricalcium phosphate (HA/TCP) scaffolds are displayed in FIG. 6. Even after only 1 hour, HOB cells are observed to be well flattened on the Sr-HT/Gahnite (20 wt %) surfaces (FIG. 7, arrows), growing many extended protrusions covering most of the scaffold surface. In contrast, Sr-HT and HA/TCP displayed fewer cells which remained much more contracted at 1 h. At 24 h, spreading was maintained at high levels for the Sr-HT-20% Gahnite and remained more extensive than that observed for the other materials. Substantially reduced spreading was observed compared to the newly developed Sr-HT/Gahnite (20 wt %). These results confirm the biocompatibility of the developed scaffold and indicate excellent promotion of osteoblast adhesion. Numbers of cells and degree of flattening appears markedly superior to the Sr-HT and to the commercially used HA/TCP.

Cell Differentiation

In order to validate the biocompatibility of the material of the invention, Sr-HT-Gahnite (5 wt %), Sr-HT-Gahnite (11 wt %), Sr-HT-Gahnite (14 wt %) and Sr-HT/Gahnite (20 wt %) were prepared and the cell differentiation results were compared to the results of cells seeded on Sr-HT and HA/TCP scaffolds for 1 and 24 h, and their expression of key osteoblast differentiation markers (Runx-2 and osteocalcin) and were compared to clinically used HA/TCP scaffolds and the Sr-HT scaffolds. Runx-2 is an early master transcription factor in osteoblast differentiation while osteocalcin is a late marker of osteoblast differentiation. Results showed that osteogenic gene expression in HOBs seeded on Sr-HT-Gahnite (14 wt %) and Sr-HT/Gahnite (20 wt %) scaffolds were significantly upregulated for both Runx-2 and for osteocalcin at day 1 (see, FIG. 7) compared to HA/TCP and Sr-HT scaffolds. These results indicate that Sr-HT/Gahnite (20 wt %) scaffolds actively support osteoblast differentiation and indicate a high potential for osteoconductivity in vivo.

Material Characterisation

The material properties of Sr-HT/20% Gahnite have been further characterised by scanning electron microscopy which confirms the presence of two phases in this material.

Figure 10A:
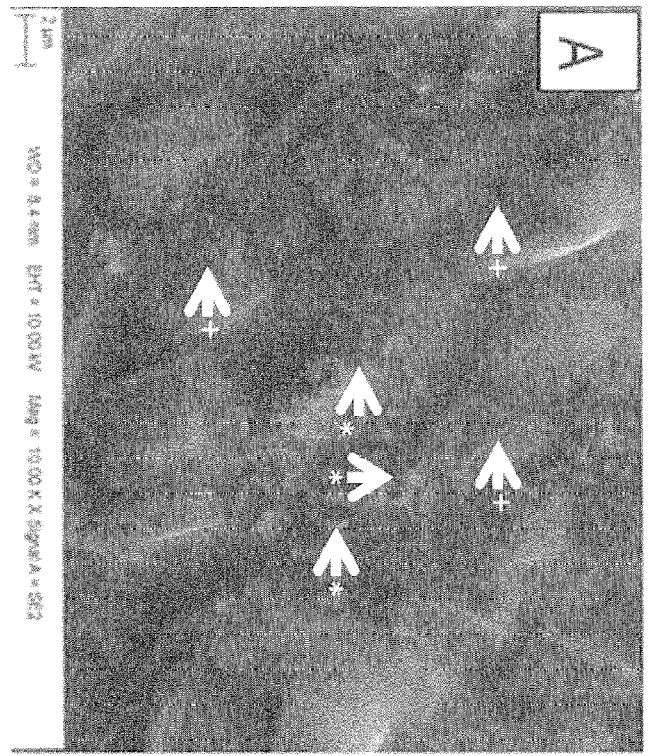
FIG. 10A shows scanning electron microscopy of the surface of Sr-HT scaffolds and FIG. 10B shows a backscatter image of Sr-HT/20% Gahnite scaffolds, which confirm the presence of two crystalline phases of HT (arrows marked with "+") and $ZnAl_2O_4$ crystals (arrows marked with "*")
Figure 10B:
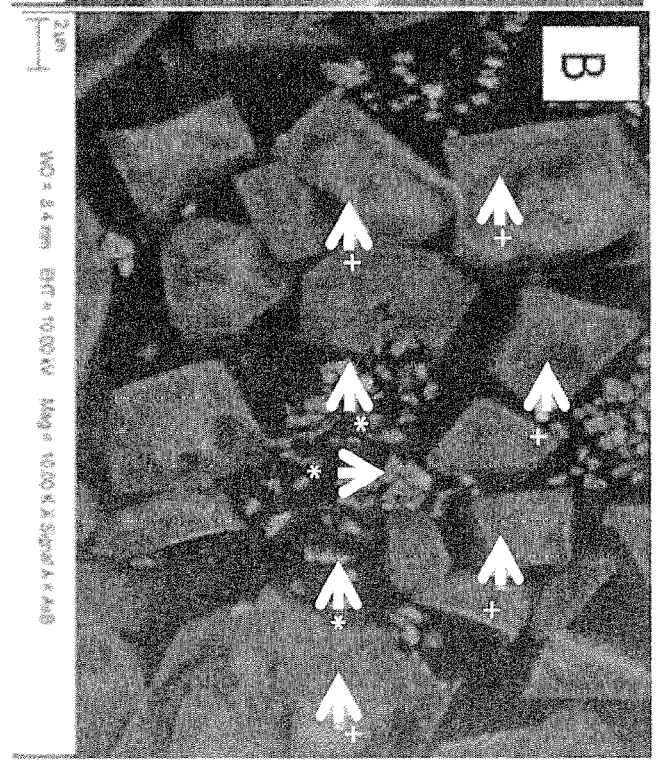
Figure 11A:
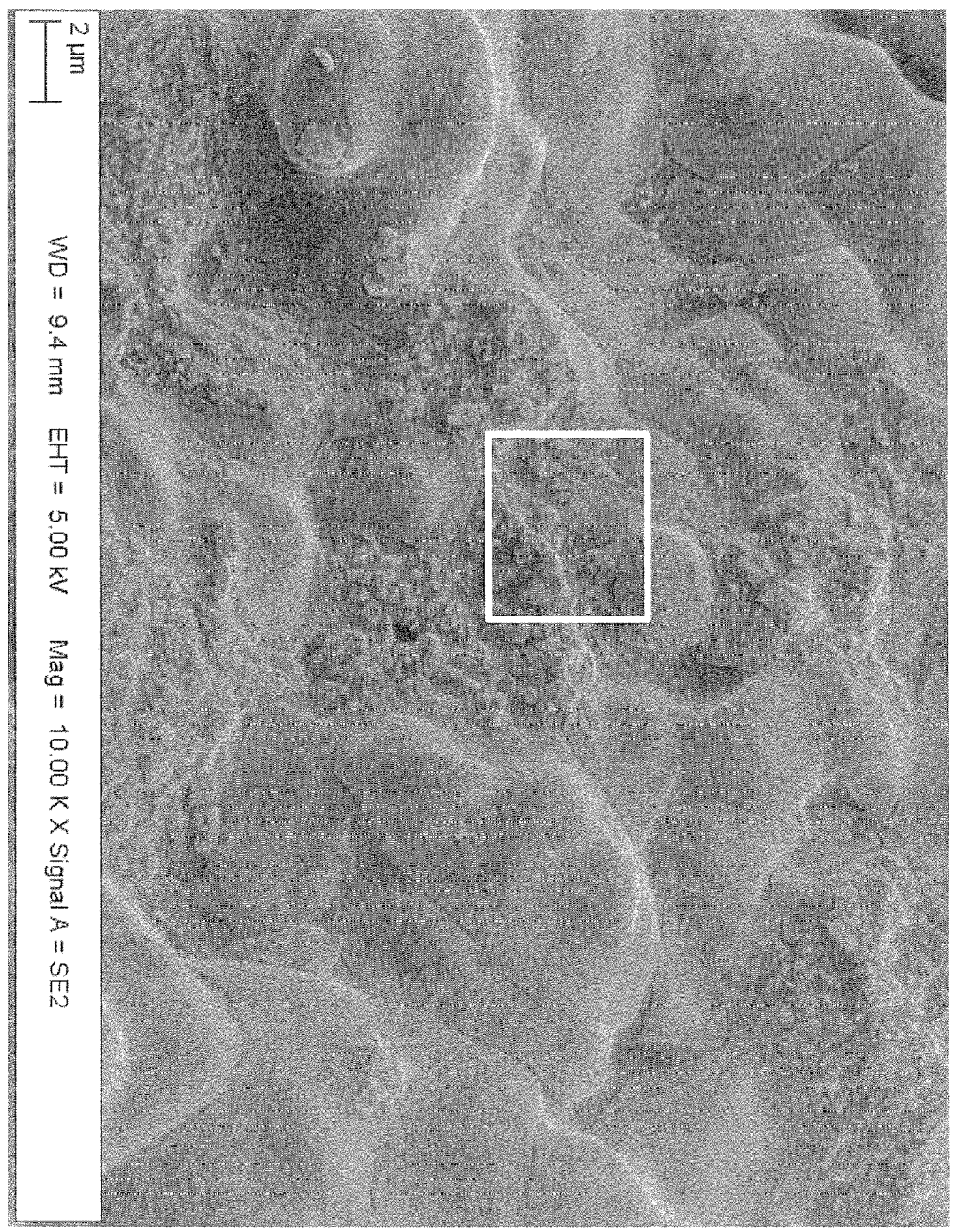
FIG. 11 shows surface changes of Sr-HT/20% Gahnite after soaking in simulating body fluid (SBF) for 7 days (A, A'), 14 days (B, B') and 28 days (C, C'), wherein Figures labelled A', B' and C' are the "boxed" regions of the respective Figures A, B and C shown at higher magnification.
Figure 11A:
Figure 11B:
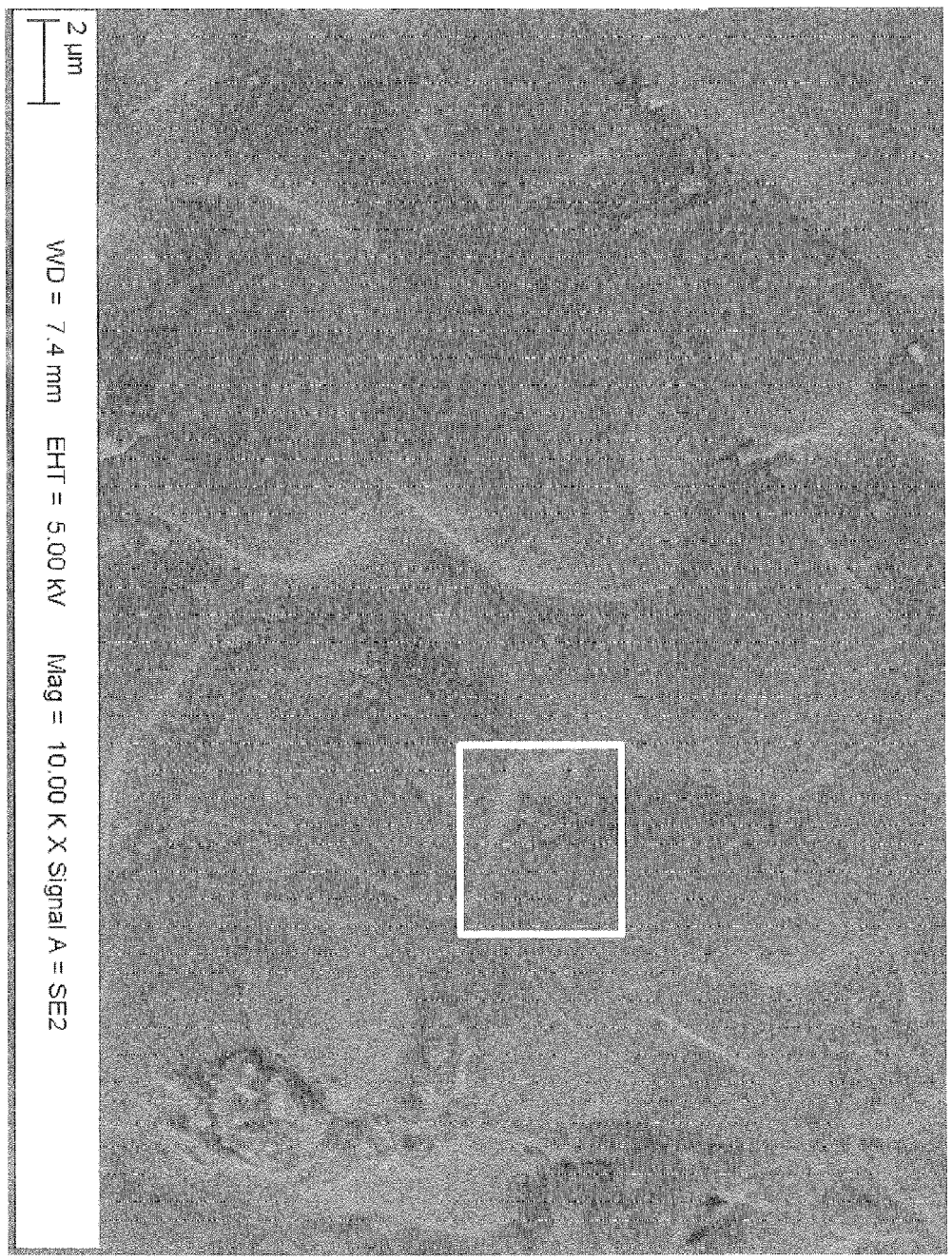
Figure 11B:
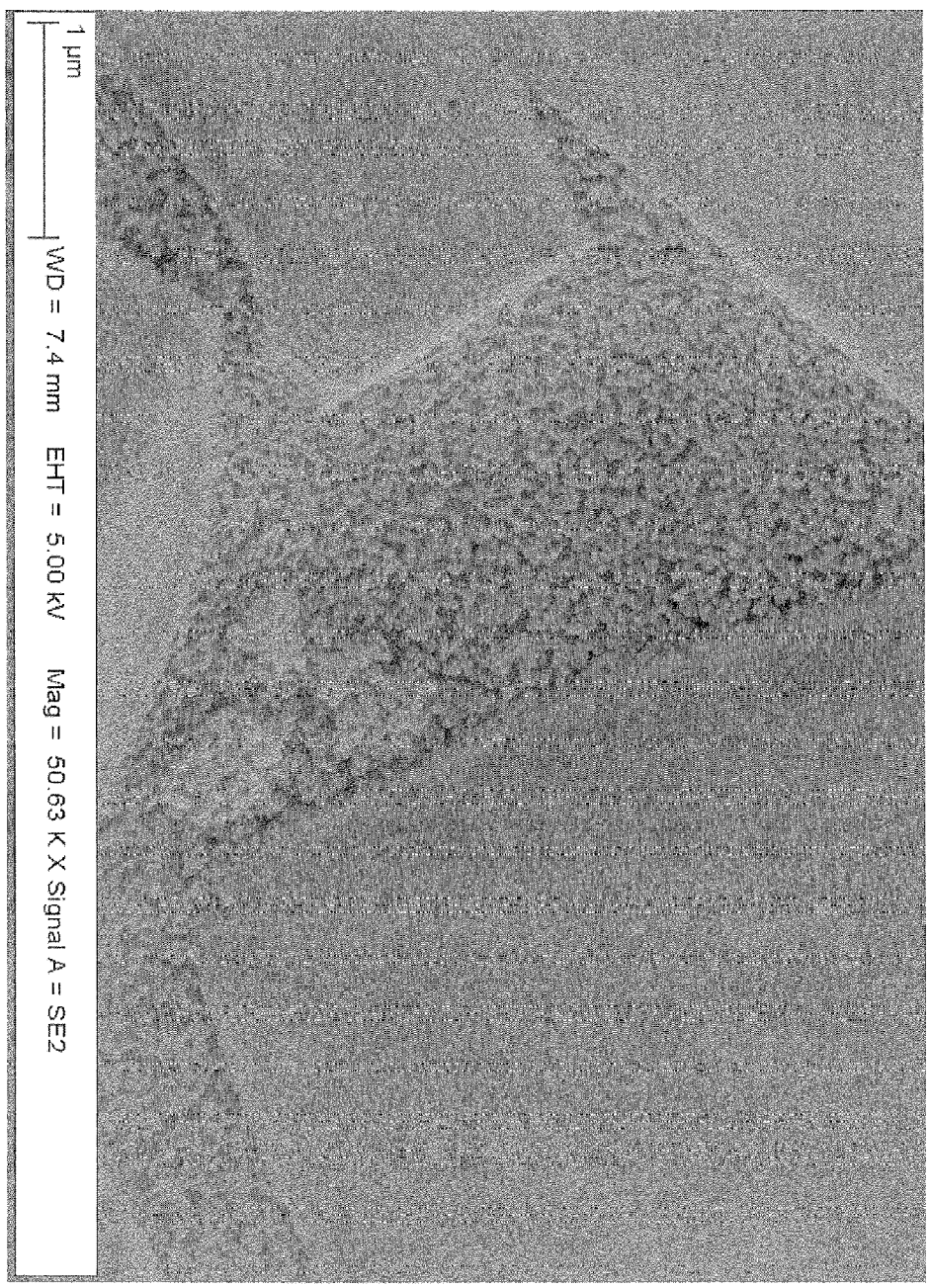
Figure 11C:
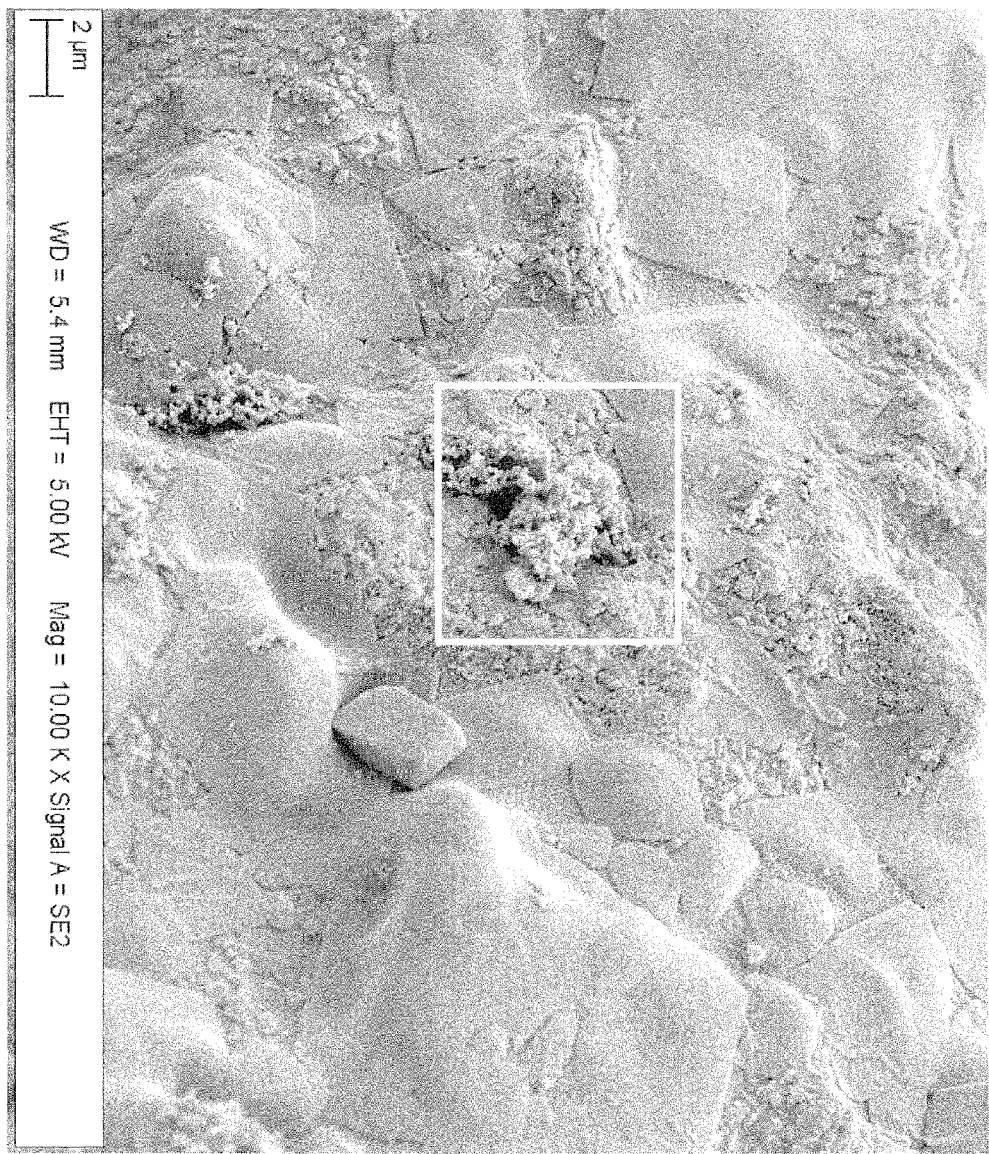
Figure 11C:
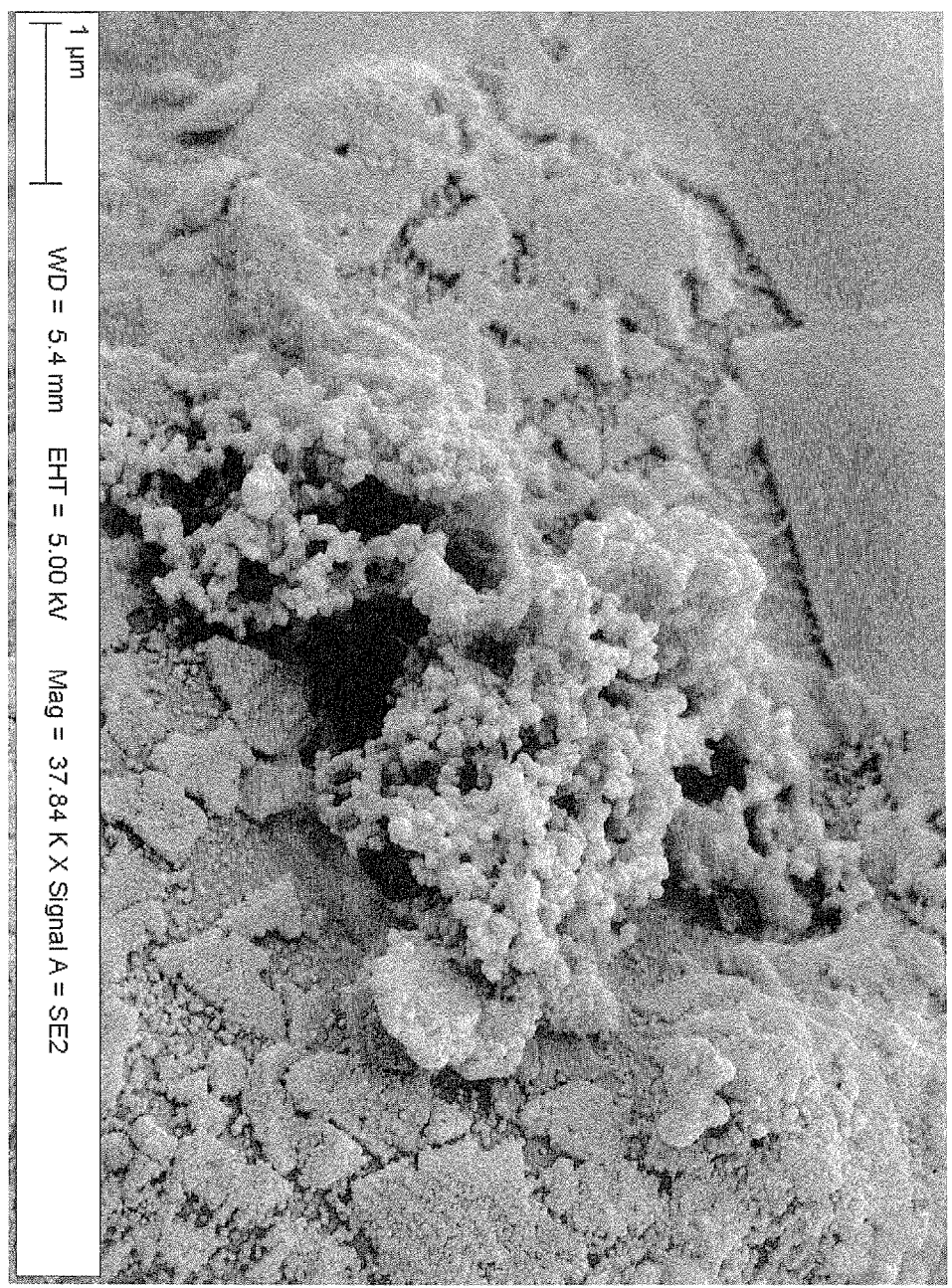

FIG. 10A shows scanning electron microscopy of surface of Sr-HT scaffolds and FIG. 10B shows backscatter imaging of Sr-HT/20% Gahnite scaffolds. Backscatter imaging of Sr-HT/20% Gahnite scaffolds confirm the presence of two crystalline phases of SrHT and gahnite ($ZnAl_2O_4$) crystals. In addition to the two crystal phases, there is an amorphous glass component (sometimes called a "glass phase") between the crystal phases or grains, which appears as the dark material in the back scatter image.

Effects on Apatite Crystal Formation of Soaking Sr-HT/20% Gahnite Scaffolds in Simulating Body Fluid.

The formation of apatite crystals on the surface of ceramic materials following soaking is simulating body fluid is predictive of bio-activity in vivo (Kokubo T. and Takadama H, "How useful is SBF in predicting in vivo bone bioactivity?", Biomaterials, (2006) 27, 2907-2915). A study has been conducted on the effects of soaking Sr-HT/20% Gahnite scaffolds in simulated body fluid, which demonstrate the progressive formation of apatite crystals on the ceramic surface, providing further evidence for the bioactivity and clinical utility of the material of the invention.

FIG. 11 shows surface changes of Sr-HT/20% Gahnite after soaking in simulating body fluid (SBF) for 7 days (A, A'), 14 days (B, B') and 28 days (C, C'). Figures labelled 11A', B', and C' are the respective regions of FIGS. 11A, B and C shown at higher magnification. After soaking Sr-HT/20% Gahnite scaffolds in SBF for 7 days, degradation of the scaffold started at the grain boundaries. After 14 days, nucleation of apatite crystals can be detected in this region. By 28 days, nano-sized apatite crystals had grown and covered the surface of the scaffold, especially at grain boundaries. At this point, glass phase and $ZnAl_2O_4$ crystals in the surface were completely degraded and transformed to apatite crystals.

Figure 12:
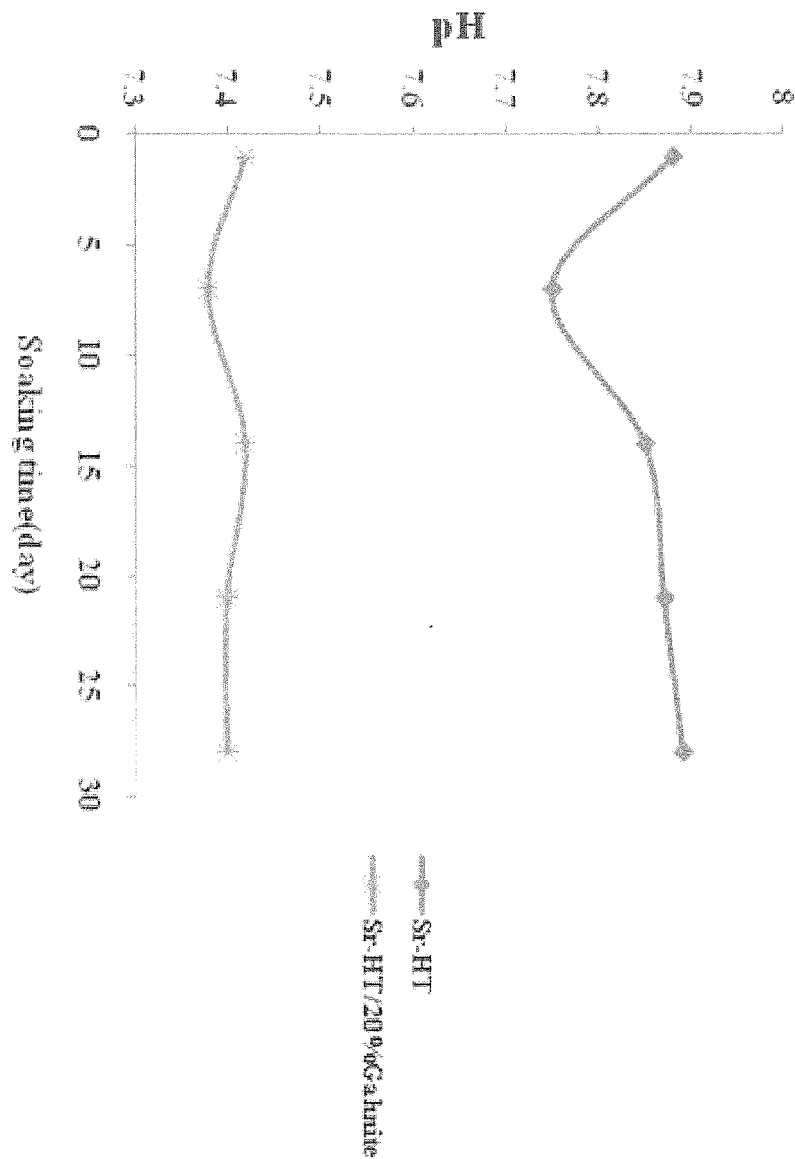
FIG. 12 shows time-dependent pH changes in simulating body fluid after soaking the prepared scaffolds, which demonstrates the superiority of Sr-HT/20% Gahnite in maintaining physiological pH levels (pH 7.4)

One of the drawbacks of calcium silicate based ceramics is the production of alkaline degradation products when placed in aqueous solutions such as simulating body fluid. These can lead to local increases in pH around implants resulting in tissue injury and death. Sr-HT/20% Gahnite ceramics do not induce an increase in pH but instead aqueous fluids in contact with these materials are maintained at the physiological pH 7.4 indicating greater potential biocompatibility (see, FIG. 12).

In Vivo Assessment of Sr-HT-20% Gahnite

Highly porous and interconnected scaffolds were prepared comprising Sr-HT/20% Gahnite or the clinically used material tricalcium phosphate/hydroxyapatite (TCP/HA), using the fully reticulated polyurethane foam as the sacrificial template to produce the scaffold structure, as previously described (Roohani-Esfahani S. I. et al., Biomaterials, 2010 July; 31 (21) 5498-509, 2010).

Surgical Preparation

In vivo effectiveness of Sr-HT/20% Gahnite, compared to TCP/HA was assessed by implantation of porous scaffolds into critical sized defects generated through the radius of rabbits. The ulna provides significant mechanical support in this model however partial weight bearing is transmitted to the scaffold.

A 2.5 cm incision was made on the dorsomedial aspect of the forearm mid way between the elbow and carpus. A sterile ruler was used to measure 1.5 cm proximal to this initial cut, and the soft tissues were retracted and a periosteal elevator was placed palmarly, and a second cut made in the radius. Hemostasis was performed prior to insertion of the implant into the 1.5 cm bone defect. TCP/HA (n=6) and 6 Sr-HT/20% Gahnite (n=6) were implanted one implant per rabbit (see, FIG. 13). Following placement of the implant, the wound was closed. The rabbits were subsequently recovered and maintained for 12 weeks with ample space for exercise.

At 12 weeks the operated limbs were x-rayed harvested, and evaluated for histomorphometric evaluation using undecalcified techniques.

Figures 13A, 13B:
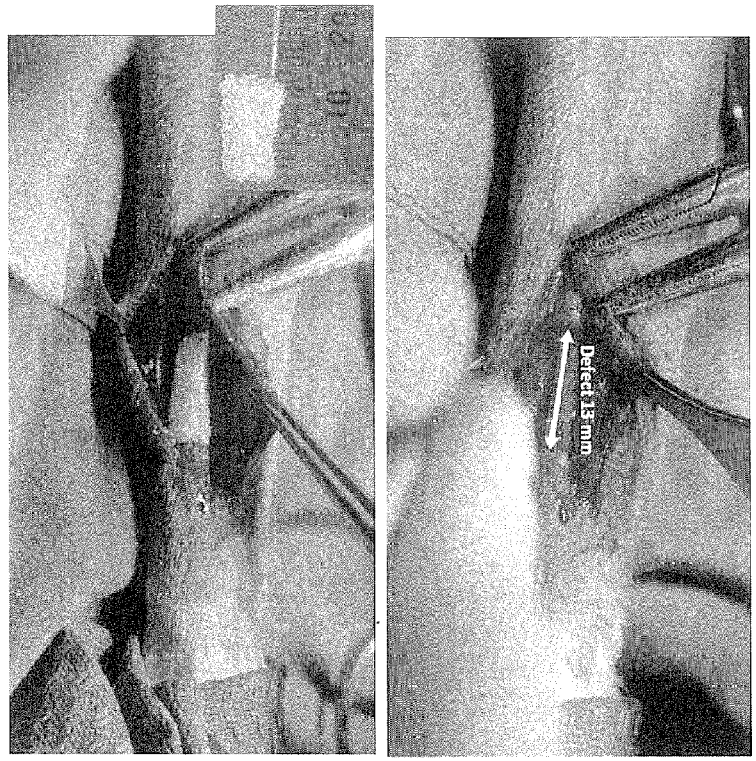
FIG. 13A shows the dimensions of the bone defect produced in the rabbit radius.
FIG. 13B shows the placement of the scaffold within the defect (insert shows scaffold prior to insertion)
Figure 13C:
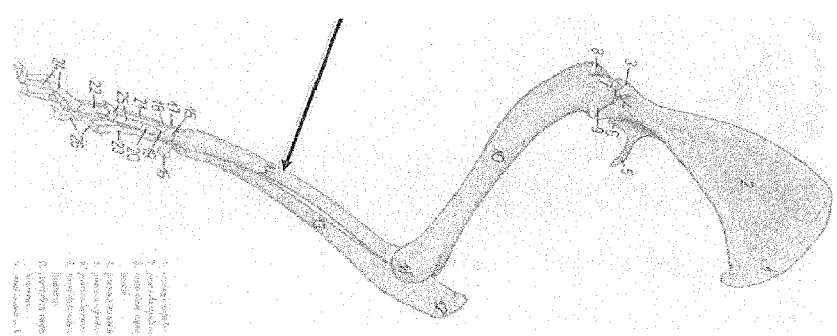
FIG. 13C (arrow) shows the anatomic location of the defect on the rabbit forelimb.

FIG. 13 shows scaffolds implanted in the rabbit radial load-bearing critical size defect. FIG. 13A shows the dimensions of the bone defect produced in the rabbit radius. FIG. 13B shows the placement of the scaffold within the defect (insert shows scaffold prior to insertion). FIG. 13C shows the anatomic location of the defect on the rabbit forelimb.

Figure 14:
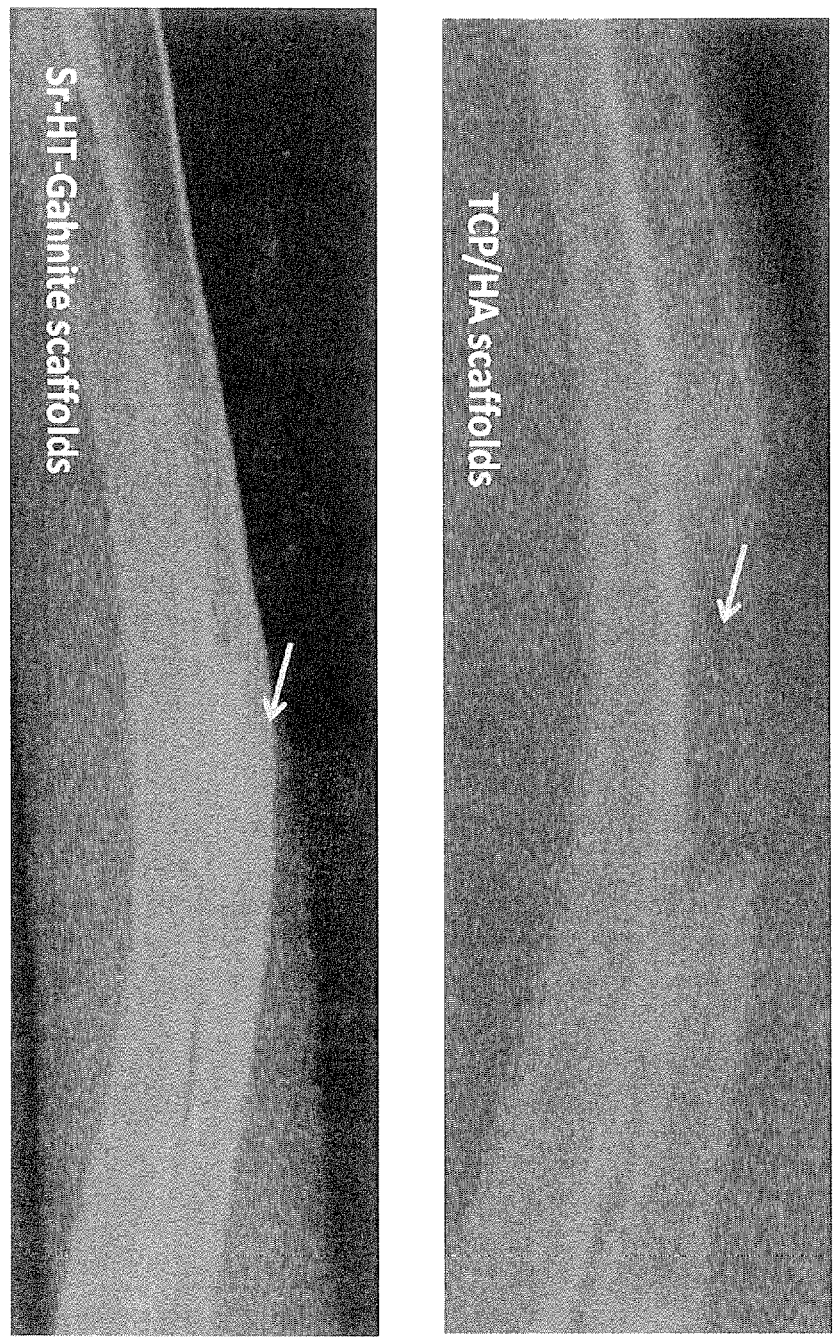
FIG. 14 shows radiographically Sr-HT/20% Gahnite (referred to in the Figure as "Sr-HT-Gahnite scaffolds", lower image) showing complete bridging of the defect at 12 weeks, which is compared to the clinically used TCP/HA (upper image)

The Sr-HT/20% Gahnite scaffolds generated extensive new bone formation completely bridging the defect as can be seen in a representative radiograph taken 12 weeks after implantation, which is in contrast to lack of bridging with the clinically used material TCP/HA (see, FIG. 14). Expert blinded radiographic assessment of the repaired defects using a standard scoring system (see, Table 1) demonstrated statistically significant improved bridging of the defects with Sr-HT/20% Gahnite compared to TCP (see, FIG. 15).

TABLE 1

Method for radiological scoring employed in this study

| Criteria | Score |
| --- | --- |
| No obvious bone regeneration | 0 |
| Less than 50% bone regeneration | 1 |
| More than 50% bone regeneration | 2 |
| Almost Fused | 3 |
| Fused - not full thickness | 4 |
| Fused - full thickness | 5 |

FIG. 14 shows a radiographic analysis of Sr-HT/20% Gahnite (referred to in the figure as 'Sr-HT-Gahnite scaffold') showing complete bridging of the defect at 12 weeks, compared to the clinically used TCP/HA. In these representative radiographs the defect (arrow) can be seen to be translucent with TCP/HA indicating no bridging of the defect. In contrast, the bone defect for Sr-HT/20% Gahnite is seen to contain new bone bridging the entire defect.

Figure 15:
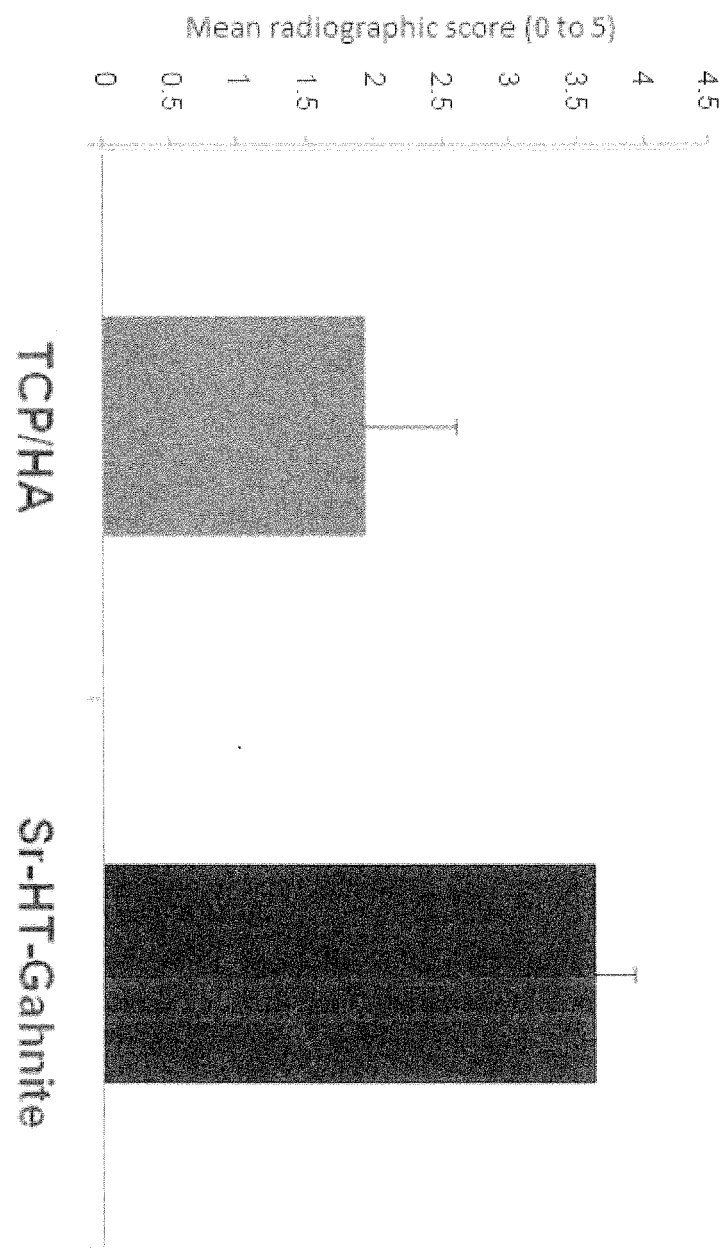
FIG. 15 shows radiographic scoring of defect bridging being superior for the Sr-HT/20% Gahnite (referred to in the Figure as "Sr-HT-Gahnite") based scaffolds compared to TCP/HA.

FIG. 15 shows radiographic scoring of defect bridging was superior of the defect for Sr-HT/20% Gahnite (referred to in the Figure as 'Sr-HT-Gahnite') based scaffolds compared to TCP/HA. Scoring of the radiographs was conducted by two independent veterinary experts blinded to the ceramic used according to a standard scoring system. Significantly higher scores for defect bridging were obtained for Sr-HT/20% Gahnite based scaffolds compared to TCP/HA.

Histological Assessment of Defect Bridging and New Bone Formation

Undecalcified histological assessment was conducted to assess the presence of bone bridging the radial defects containing either TCP/HA or Sr-HT/20% Gahnite. Sections were taken adjacent to the edge of the defect and at its midpoint. Bone formation was assessed qualitatively at each site and quantitatively at the midpoint by histomorphometry using standard techniques. Extensive new bone formation was observed at both the defect edge and at the midpoint for Sr-HT/20% Gahnite indicating complete defect bridging. In contrast, very little new bone formation was seen for TCP/HA (see, FIG. 16). In addition, scaffold architecture was significantly better preserved for Sr-HT/20% Gahnite, which is consistent with its superior mechanical properties. The appearance of marrow spaces (see, arrows) within the Sr-HT/20% Gahnite scaffolds indicate bone remodelling is occurring and normal cortical architecture is being regenerated. Histomorphometric assessment at the midpoint of the defects confirmed a significantly increased level of bone formation in the Sr-HT/20% Gahnite treated defects compared to TCP/HA (see, FIG. 17).

Figure 16:
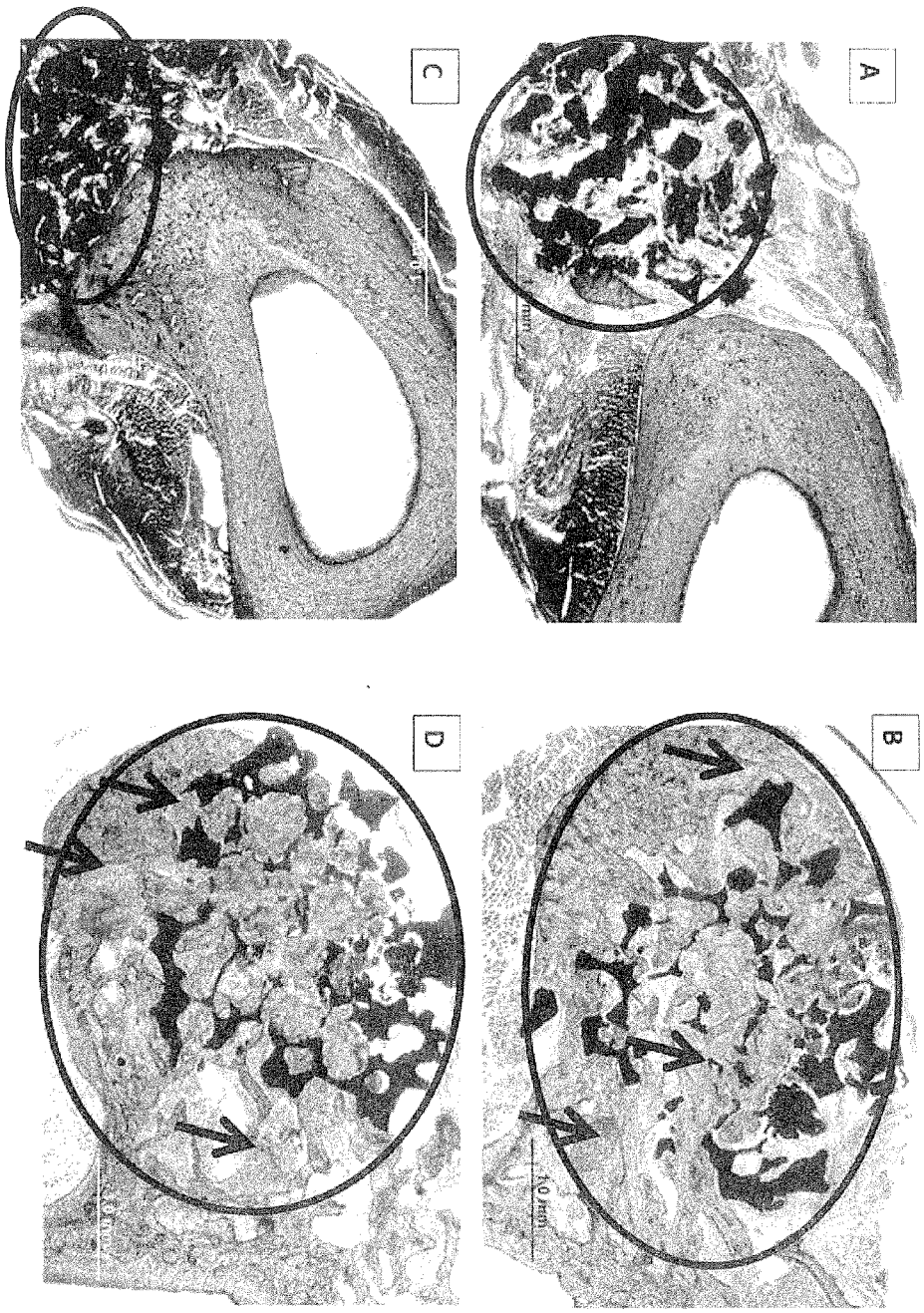
FIG. 16 shows representative undecalcified histological bone sections demonstrating that Sr-HT/20% Gahnite (FIGS. 16B and 16D) induces superior new bone formation compared to compared to TCP/HA (FIGS. 16A and 16C)

FIG. 16 shows representative undecalcified histological bone sections which demonstrate that Sr-HT/20% Gahnite (FIG. 16B and FIG. 16D) induces superior new bone formation. The area of the generated defect is circled in each micrograph. The remaining bone to the right side of each image is the original ulna which had no defect introduced. Increased amounts of new bone growing throughout the scaffolds (black material on the figures) is observed in the rabbit radius defects treated with Sr-HT/20% Gahnite (FIG. 16B and FIG. 16D) compared to TCP/HA (FIG. 16A and FIG. 16C) at both defect midpoint and edges (A and B are sections taken from the midpoint of the defect while C and D were from the edge of the defect). The architecture of the Sr-HT/20% Gahnite scaffold is preserved consistent with its increased mechanical strength, whereas scaffold compression is observed for TCP/HA. The appearance of marrow spaces (arrows) within the Sr-HT/20% Gahnite scaffolds (FIG. 16B and FIG. 16D) indicate bone remodeling is occurring and normal cortical architecture is being regenerated.

Figure 17:
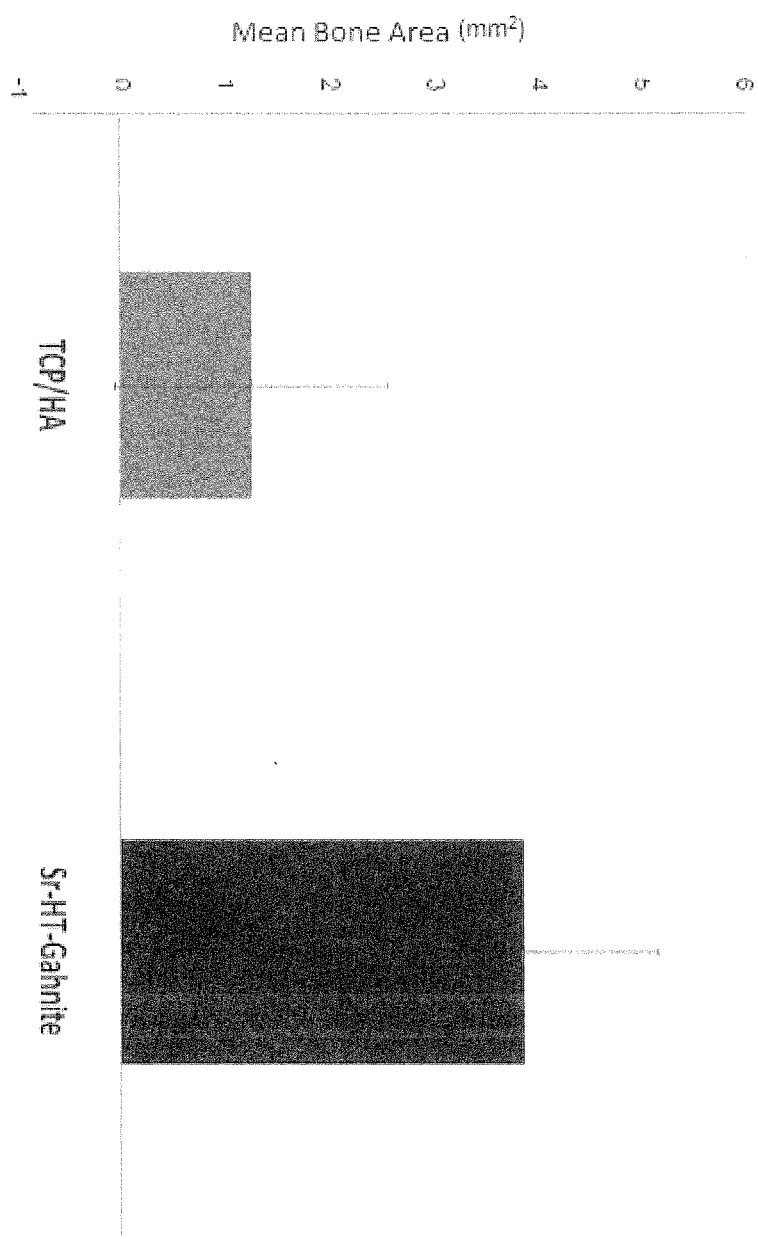
FIG. 17 shows histomorphometric measurements demonstrating that Sr-HT/20% Gahnite (referred to in the Figure as "Sr-HT-Gahnite") shows superior formation of new bone at the mid-point of the radial defect indicating effective bridging of the bone defect.

FIG. 17 shows histomorphometric measurements demonstrating that Sr-HT/20% Gahnite (referred to in the Figure as 'Sr-HT-Gahnite') had superior formation of new bone at the mid-point of the radial defect, indicating effective bridging of the bone defect. Undecalcified sections from the midpoint of the defect were stained with toluidine blue to highlight new bone. The region of the defect was defined and new bone within this region measured using Image J software (NIH, USA). Significantly greater areas of new bone were observed for Sr-HT/20% Gahnite compared to that for TCP/HA indicating more effect defect bridging.

In conclusion, the composite ceramic material of the present invention shows favourable bio-ceramic properties with increased bending strength and fracture toughness. It also shows improved biological properties.

Although the invention has been described with reference to specific examples, it will be appreciated by those skilled in the art that the invention may be embodied in many other forms. In particular, features of any one of the various described examples may be provided in any combination in any of the other described examples.

The claims defining the invention are as follows:

1. A composite biocompatible ceramic material comprising a first and a second phase, wherein said first phase is doped hardystonite ($Ca_2ZnSi_2O_7$) and said second phase is a metal oxide belonging to the spinel group of minerals.

2. A material according to claim 1, wherein said hardystonite is doped with at least one of strontium, barium or magnesium.

3. A material according to claim 1, wherein said first phase comprises a molecular formula $[(Sr_aBa_bMg_c)Ca_{[2.0-\Sigma(a, b, c)]}ZnSi_2O_7]$, wherein $\Sigma(a, b, c)$ is between 0.05 and 0.9; and wherein the second phase comprises a molecular formula $[(Mg_xZn_yFe_z)Al_2O_4]$, wherein $\Sigma(x, y, z)=1$.

4. A material according to claim 1, wherein said first phase is a strontium calcium zinc silicate of the formula $Sr_{0.1}Ca_{1.9}ZnSi_2O_7$.

5. A material according to claim 1, wherein said metal oxide is gahnite ($ZnAl_2O_4$), spinel ($MgAl_2O_4$), hercynite ($FeAl_2O_4$), or combinations thereof.

6. A material according to claim 1, wherein the weight percentage of said first phase is between 70 and 99%.

7. A material according to claim 6, wherein the respective weight percentage of said second phase is between 30 and 1%.

8. A material according to claim 1, wherein the material is an implant grade or medical grade material.

9. A material according to claim 1, wherein the material forms a hydroxyapatite layer upon exposure to bodily fluids, thereby to enhance biocompatibility within a mammalian body.

10. A material according to claim 1, wherein said material is suited for the regeneration of bone and other tissue, or for resurfacing arthritic joints to promote the growth of articular cartilage, or for the development of 3D scaffolds which promote migration, proliferation and differentiation of bone and endothelial cells, or for orthopaedic and maxillofacial surgeries, or for load-bearing parts, or to support bone tissue regeneration/formation and vascularisation, or for scaffolds for osteochondral defects, or as a coating on currently-used orthopaedic and dental implants to provide enhanced long-term implant stability, or for cosmetic purposes.

11. A material according to claim 1, wherein the porosity of said material is between 20 and 80%.

12. A material according to claim 1, wherein the pore size of said material is between 20 and 500 microns.

13. A material according to claim 1, wherein the compressive strength of said material is between 2 and 15 MPa.

14. A material according to claim 1, comprising a coating with at least one resorbable polymer material, selected from polyglycolides, polydioxanones, polyhydroxyalkanoates, polylactides, alginates, collagens, chitosans, polyalkylene oxalate, polyanhydrides, poly(glycolide-co-trimethylene carbonate), polyesteramides, and/or polydepsipeptides.

15. A composite biocompatible ceramic material comprising a first and a second phase, wherein said first phase comprises calcium zinc silicate doped with an element selected from the group of dopants consisting of Sr, Mg, Ba or a combination thereof; and the second phase comprises a metal aluminum oxide, wherein the metal is chosen from Mg, Zn, Fe or a combination thereof.

16. A material according to claim 15, wherein said first phase comprises a molecular formula $[Sr_xCa_{(2-x)}ZnSi_2O_7]$, wherein x is between 0.05 and 0.9.

17. A material according to claim 15, wherein said first phase comprises the molecular formula $[Sr_{0.1}Ca_{1.9}ZnSi_2O_7]$.

18. A material according to claim 15, wherein said second phase is gahnite ($ZnAl_2O_4$).

19. A material according to claim 15, wherein said calcium is at least partially substituted with magnesium.

20. A composite biocompatible ceramic material comprising strontium calcium zinc silicate and gahnite ($ZnAl_2O_4$).

21. A material according to claim 20, comprising strontium calcium zinc silicate of the approximate molecular formula $Sr_{0.1}Ca_{1.9}ZnSi_2O_7$ and gahnite.

22. An implantable medical device, a bone implant, a tooth filling, or a biocement comprising a composite biocompatible ceramic material defined according to claim 1.

23. The material according to claim 10, wherein said cosmetic purpose is nose enhancement, chin enhancement or leg lengthening.

* * * * *